(12) United States Patent
Kaduchak et al.

(10) Patent No.: US 9,074,979 B2
(45) Date of Patent: Jul. 7, 2015

(54) ULTRASONIC ANALYTE CONCENTRATION AND APPLICATION IN FLOW CYTOMETRY

(75) Inventors: Gregory Kaduchak, Los Alamos, NM (US); Greg Goddard, Los Alamos, NM (US); Gary Salzman, White Rock, NM (US); Dipen Sinha, Los Alamos, NM (US); John C. Martin, Los Alamos, NM (US); Christopher Kwiatkowski, Los Alamos, NM (US); Steven Graves, San Juan Pueblo, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 25 days.

(21) Appl. No.: 13/618,237

(22) Filed: Sep. 14, 2012

(65) Prior Publication Data

US 2013/0014826 A1 Jan. 17, 2013

Related U.S. Application Data

(63) Continuation of application No. 11/982,042, filed on Oct. 31, 2007, which is a continuation of application No. 10/979,065, filed on Nov. 2, 2004, now Pat. No. 7,340,957.

(60) Provisional application No. 60/592,169, filed on Jul. 29, 2004.

(51) Int. Cl.
*G01H 17/00* (2006.01)
*G01N 15/14* (2006.01)
(Continued)

(52) U.S. Cl.
CPC .... *G01N 15/1459* (2013.01); *G01N 2001/4094* (2013.01); *G01N 2015/1413* (2013.01); *G01N 2015/142* (2013.01)

(58) Field of Classification Search
CPC .............. G01H 17/00; G01N 15/1459; G01N 2001/4094; G01N 2015/142; G01N 2015/1413; G01N 2015/1081; G01N 2015/1087; G01N 2015/1093; G01N 2001/4077
USPC .............................................. 73/570.5, 61.75
See application file for complete search history.

(56) References Cited

U.S. PATENT DOCUMENTS 2,900,536 A   8/1959  Palo
3,882,732 A   5/1975  Fletcher et al.
(Continued)

FOREIGN PATENT DOCUMENTS

CN   1493831 A   5/2004
CN   1524948     9/2004
(Continued)

OTHER PUBLICATIONS

Aboobaker, N. et al., "Mathematical modeling of the movement of suspended particles subjected to acoustic and flow fields", *App. Math. Modeling*, 2005, 29, 515-532.
(Continued)

*Primary Examiner* — Laura Martin
*Assistant Examiner* — Rose M Miller
(74) *Attorney, Agent, or Firm* — Baker & Hostetler LLP

(57) ABSTRACT

The present invention includes an apparatus and corresponding method for concentrating analytes within a fluid flowing through a tube using acoustic radiation pressure. The apparatus includes a function generator that outputs a radio frequency electrical signal to a transducer that transforms the radio frequency electric signal to an acoustic signal and couples the acoustic signal to the tube. The acoustic signal is converted within the tube to acoustic pressure that concentrates the analytes within the fluid.

31 Claims, 17 Drawing Sheets

(51) Int. Cl.
*G01N 15/06* (2006.01)
*G01N 1/40* (2006.01)

(56) References Cited

U.S. PATENT DOCUMENTS

| | | | |
|---|---|---|---|
| 4,055,491 A | 10/1977 | Porath-Furedi |
| 4,265,124 A | 5/1981 | Lim et al. |
| 4,285,810 A | 8/1981 | Kirkland et al. |
| 4,350,683 A | 9/1982 | Galfre et al. |
| 4,434,230 A | 2/1984 | Ritts, Jr. |
| 4,492,752 A | 1/1985 | Hoffman et al. |
| 4,523,682 A | 6/1985 | Barmatz et al. |
| 4,523,982 A | 6/1985 | Lee |
| 4,596,464 A | 6/1986 | Hoffman et al. |
| 4,604,542 A | 8/1986 | Thompson |
| 4,673,512 A | 6/1987 | Schram |
| 4,743,361 A | 5/1988 | Schram |
| 4,759,775 A | 7/1988 | Peterson et al. |
| 4,777,823 A | 10/1988 | Barmatz et al. |
| 4,790,653 A | 12/1988 | North, Jr. |
| 4,845,025 A | 7/1989 | Lary et al. |
| 4,867,559 A | 9/1989 | Bach |
| 4,877,516 A | 10/1989 | Schram |
| 4,913,883 A | 4/1990 | Imai et al. |
| 4,964,303 A | 10/1990 | Barmatz et al. |
| 4,979,824 A | 12/1990 | Mathies et al. |
| 4,987,086 A | 1/1991 | Brosnan et al. |
| 4,991,923 A | 2/1991 | Kino et al. |
| 5,006,266 A | 4/1991 | Schram |
| 5,030,002 A | 7/1991 | North, Jr. |
| 5,032,381 A | 7/1991 | Bronstein et al. |
| 5,040,890 A | 8/1991 | North, Jr. |
| 5,079,959 A | 1/1992 | Miyake et al. |
| 5,085,783 A | 2/1992 | Feke et al. |
| 5,106,187 A | 4/1992 | Bezanson |
| 5,164,094 A | 11/1992 | Stuckart |
| 5,225,089 A | 7/1993 | Benes et al. |
| 5,264,906 A | 11/1993 | Ferer et al. |
| 5,346,670 A | 9/1994 | Renzoni et al. |
| 5,376,551 A | 12/1994 | Yoshikami |
| 5,395,588 A | 3/1995 | North, Jr. et al. |
| 5,430,541 A | 7/1995 | Sapp |
| 5,491,344 A | 2/1996 | Kenny et al. |
| 5,504,337 A | 4/1996 | Lakowicz et al. |
| 5,527,460 A | 6/1996 | Trampler et al. |
| 5,528,045 A | 6/1996 | Hoffman et al. |
| 5,547,849 A | 8/1996 | Baer et al. |
| 5,626,767 A | 5/1997 | Trampler et al. |
| 5,644,388 A | 7/1997 | Maekawa et al. |
| 5,674,698 A | 10/1997 | Zarling et al. |
| 5,688,406 A | 11/1997 | Dickinson et al. |
| 5,690,895 A | 11/1997 | Matsumoto et al. |
| 5,711,888 A | 1/1998 | Trampler et al. |
| 5,739,902 A | 4/1998 | Gjelsnes et al. |
| 5,798,222 A | 8/1998 | Goix |
| 5,800,861 A | 9/1998 | Chiang et al. |
| 5,831,166 A | 11/1998 | Kozuka et al. |
| 5,915,925 A | 6/1999 | North |
| 5,981,180 A | 11/1999 | Chandler et al. |
| 5,999,256 A | 12/1999 | Jones |
| 6,003,388 A | 12/1999 | Oeftering |
| 6,055,859 A | 5/2000 | Kozuka et al. |
| 6,074,879 A | 6/2000 | Zelmanovic et al. |
| 6,090,295 A | 7/2000 | Raghavarao et al. |
| 6,161,435 A | 12/2000 | Bond et al. |
| 6,197,593 B1 | 3/2001 | Deka et al. |
| 6,216,538 B1 | 4/2001 | Yasuda et al. |
| 6,221,258 B1 | 4/2001 | Feke et al. |
| 6,228,652 B1 | 5/2001 | Rodriguez et al. |
| 6,248,590 B1 | 6/2001 | Malachowski |
| 6,255,118 B1 | 7/2001 | Alfano et al. |
| 6,309,886 B1 | 10/2001 | Ambrose et al. |
| 6,332,541 B1 | 12/2001 | Coakley et al. |
| 6,348,687 B1 | 2/2002 | Brockmann et al. |
| 6,373,567 B1 | 4/2002 | Wise et al. |
| 6,449,563 B1 | 9/2002 | Dukhin et al. |
| 6,467,350 B1 | 10/2002 | Kaduchak et al. |
| 6,532,061 B2 | 3/2003 | Ortyn et al. |
| 6,549,275 B1 | 4/2003 | Cabuz et al. |
| 6,565,727 B1 | 5/2003 | Shenderov et al. |
| 6,592,821 B1 | 7/2003 | Wada et al. |
| 6,604,435 B2 | 8/2003 | Buchanan et al. |
| 6,644,118 B2 | 11/2003 | Kaduchak et al. |
| 6,647,739 B1 | 11/2003 | Kim |
| 6,668,664 B1 | 12/2003 | Ohkawa |
| 6,683,314 B2 | 1/2004 | Oostman, Jr. et al. |
| 6,713,019 B2 | 3/2004 | Ozasa et al. |
| 6,736,904 B2 | 5/2004 | Poniatowski et al. |
| 6,773,556 B1 | 8/2004 | Brockie et al. |
| 6,794,671 B2 | 9/2004 | Nicoli et al. |
| 6,797,158 B2 | 9/2004 | Feke et al. |
| 6,813,017 B1 | 11/2004 | Hoffman et al. |
| 6,816,257 B2 | 11/2004 | Goix |
| 6,831,279 B2 | 12/2004 | Ho |
| 6,881,314 B1 | 4/2005 | Wang et al. |
| 6,911,082 B2 | 6/2005 | Sato et al. |
| 6,929,750 B2 | 8/2005 | Laurell et al. |
| 6,949,355 B2 | 9/2005 | Yamanishi et al. |
| 6,982,165 B2 | 1/2006 | Yamakawa et al. |
| 7,008,540 B1 | 3/2006 | Weavers et al. |
| 7,018,819 B2 | 3/2006 | Orwar et al. |
| 7,047,809 B2 | 5/2006 | Cobb |
| 7,052,864 B2 | 5/2006 | Durkop et al. |
| 7,064,823 B2 | 6/2006 | Roche et al. |
| 7,069,793 B2 | 7/2006 | Ishikawa et al. |
| 7,081,192 B1 | 7/2006 | Wang et al. |
| 7,091,348 B2 | 8/2006 | O'Neill et al. |
| 7,108,137 B2 | 9/2006 | Lal et al. |
| 7,113,266 B1 | 9/2006 | Wells |
| 7,161,665 B2 | 1/2007 | Johnson |
| 7,166,443 B2 | 1/2007 | Walker et al. |
| 7,190,832 B2 | 3/2007 | Frost et al. |
| 7,205,707 B2 | 4/2007 | Masters et al. |
| 7,221,077 B2 | 5/2007 | Sawada |
| 7,255,780 B2 | 8/2007 | Shenderov |
| 7,262,838 B2 | 8/2007 | Fritz |
| 7,267,798 B2 | 9/2007 | Chandler |
| 7,315,357 B2 | 1/2008 | Ortyn et al. |
| 7,329,545 B2 | 2/2008 | Pamula et al. |
| 7,340,957 B2 | 3/2008 | Kaduchak et al. |
| 7,362,432 B2 | 4/2008 | Roth |
| 7,373,805 B2 | 5/2008 | Hawkes et al. |
| 7,403,125 B2 | 7/2008 | Rich |
| 7,431,892 B2 | 10/2008 | Zumeris et al. |
| 7,477,363 B2 | 1/2009 | Nagai |
| 7,484,414 B2 | 2/2009 | Priev et al. |
| 7,570,676 B2 | 8/2009 | Essaian et al. |
| 7,758,811 B2 | 7/2010 | Durack et al. |
| 7,804,595 B2 | 9/2010 | Matula et al. |
| 7,835,000 B2 | 11/2010 | Graves et al. |
| 7,837,040 B2 | 11/2010 | Ward et al. |
| 7,990,525 B2 | 8/2011 | Kanda |
| 8,075,786 B2 | 12/2011 | Bagajewicz |
| 8,083,068 B2 | 12/2011 | Kaduchak et al. |
| 8,134,705 B2 | 3/2012 | Kaduchak et al. |
| 8,173,413 B2 | 5/2012 | Chiu et al. |
| 8,227,257 B2 | 7/2012 | Ward et al. |
| 8,263,407 B2 | 9/2012 | Goddard et al. |
| 8,264,683 B2 | 9/2012 | Matula et al. |
| 8,266,950 B2 | 9/2012 | Kaduchak et al. |
| 8,266,951 B2 | 9/2012 | Kaduchak et al. |
| 8,309,408 B2 | 11/2012 | Ward et al. |
| 2003/0015035 A1* | 1/2003 | Kaduchak et al. ........... 73/570.5 |
| 2003/0059850 A1 | 3/2003 | Evans |
| 2005/0072677 A1 | 4/2005 | Gascoyne et al. |
| 2006/0034733 A1 | 2/2006 | Ferren et al. |
| 2006/0163166 A1 | 7/2006 | Hawkes et al. |
| 2007/0071683 A1 | 3/2007 | Dayton et al. |
| 2009/0029870 A1 | 1/2009 | Ward et al. |
| 2009/0038932 A1 | 2/2009 | Denslow et al. |
| 2009/0042239 A1 | 2/2009 | Ward et al. |
| 2009/0045107 A1 | 2/2009 | Ward et al. |
| 2009/0053686 A1 | 2/2009 | Ward et al. |
| 2009/0107241 A1 | 4/2009 | Goddard et al. |

(56) References Cited

U.S. PATENT DOCUMENTS

| | | | |
|---|---|---|---|
| 2009/0178716 A1 | 7/2009 | Kaduchak et al. | |
| 2009/0227042 A1 | 9/2009 | Gauer et al. | |
| 2010/0000325 A1 | 1/2010 | Kaduchak et al. | |
| 2010/0009333 A1 | 1/2010 | Auer | |
| 2011/0024335 A1 | 2/2011 | Ward et al. | |
| 2011/0032522 A1 | 2/2011 | Graves et al. | |
| 2011/0134426 A1 | 6/2011 | Kaduchak et al. | |

FOREIGN PATENT DOCUMENTS

| | | |
|---|---|---|
| CN | 1739020 A | 2/2006 |
| CN | 101060898 | 10/2007 |
| DE | 3027433 | 2/1982 |
| EP | 0 147 032 | 3/1985 |
| EP | 0 292 470 | 11/1988 |
| EP | 0 773 055 | 5/1997 |
| EP | 1 416 239 | 5/2004 |
| FR | 821419 | 12/1937 |
| GB | 500271 | 12/1937 |
| JP | 363139231 A | 6/1988 |
| JP | 01-112161 | 4/1989 |
| JP | 406241977 A | 9/1994 |
| JP | 07-047259 | 2/1995 |
| JP | 408266891 A | 10/1996 |
| JP | 11-014533 | 1/1999 |
| JP | 2002-22531 | 1/2002 |
| RU | 2224992 | 2/2004 |
| WO | WO 88/09210 | 12/1988 |
| WO | WO 90/05008 | 5/1990 |
| WO | WO 94/29695 | 12/1994 |
| WO | WO 97/02482 | 1/1997 |
| WO | WO 99/042810 | 8/1999 |
| WO | WO 00/41794 | 7/2000 |
| WO | WO 02/059577 | 8/2002 |
| WO | WO 02/072234 | 9/2002 |
| WO | WO 02/072236 | 9/2002 |
| WO | WO 03/079006 | 9/2003 |
| WO | WO 2004/024287 | 3/2004 |
| WO | WO 2004/033087 | 4/2004 |
| WO | WO 2004/048948 | 6/2004 |
| WO | WO 2006/031299 | 3/2006 |
| WO | WO 2006/032703 | 3/2006 |
| WO | WO 2006/076195 | 7/2006 |
| WO | WO 2007/128795 | 11/2007 |
| WO | WO 2008/122051 | 10/2008 |
| WO | WO 2009/086043 | 7/2009 |
| WO | WO 2009/091925 | 7/2009 |
| WO | WO 2011/068764 | 6/2011 |

OTHER PUBLICATIONS

Aleksandrov, et al., "Pulsed Laser Florescence Spectrometer," *Zhurnal Prikladnoi Spektroskopii*, Oct. 1987, 47(4), 686-692.

Anderson, M.J. et al., "Use of Acoustic Radiation Pressure to Concentrate Small Particles in an Air Flow," 2002 IEEE Ultrasonics Symposium, Jan. 1, 2002, 481-484.

Anderson, M. et al., "The Physics and Technology of Ultrasonic Particle Separation in Air", *WCU*, 2003, 1615-1621.

Apfel, R.E. et al., "Acoustic Radiation Pressure—Principles and Application to Separation Science", *Fortschritte Der Akustik DAGA '90*, 1990, 19-30.

Araz, M.K. et al., "Ultrasonic Separation in Microfluidic Capillaries", *IEEE Ultrasonics Symposium*, 2003, 1066-1069.

Asai, M.K. et al., "Ultrasonic Treatment of Slurry," Third International Coal Preparation Conference, 1958, 518-527.

Bardsley, et al., "Electroacoustic Productions of Murine Hybridomas," Journal of Immunological Methods, 129(1), 1990, 41-47.

Barmatz, M. et al., "Acoustic radiation potential on a sphere in plane, cylindrical, and spherical standing wave fields", *J. Acoust. Soc. Am.*, 1985, 77, 928-945.

Bauerecker, S. et al., "Formation and growth of ice particles in stationary ultrasonic fields", *J. of Chem. Phys.*, 1998, 3709-3712.

Bazou, D. et al., "Physical Environment of 2-D Animal Cell Aggregates Formed in a Short Pathlength Ultrasound Standing Wave Trap", *Ultrasound in Med. & Biol.*, 2005, 31, 423-430.

Benes, "Separation of Dispersed Particles by Ultrasonic-Induced Coagulation", 15th Conference of the German Society for Acoustics, 1989, 2 pages.

Benes, E. et al., "Improved quartz crystal microbalance technique", *J. Appl. Phys.*, 1984, 56, 608-626.

Beverloo, H.B. et al., "Inorganic Phsophors as New Luminescent Labels for Irnmunocytochernistry and Time-Resolved Microscopy", *Cytometry*, 1990, 11, 784-792.

Bienvenue, J.M. et al., "Microchip-Based Cell Lysis and DNA Extraction from Sperm Cells for Application to Forensic Analysis", *J. Forensic Sci.*, 2006, 51, 266-273.

Binks, B.P. et al., "Modern Aspects of Emulsion Science", *The Royal Society of Chemistry*, 1998, 310-321.

Bishop, J.E. et al., "Mechanism of higher brightness of PerCP-Cy5.5", *Cytometry Supp*, 2000, 10, 162-163.

Borgnis, "Acoustic Radiation Pressure of Plane Compressional Waves," *Reviews of Modern Physics*, Jul. 1953, 25(3),653-664.

Borisov, S.M. et al., "Blue LED Excitable Temperature Sensors Based on a New Eurpium (III) Chelate," *J. Fluoresc.*, 2008, 18, 581-589.

Borthwick, K.A. et al., "Development of a novel compact sonicator for cell disruption", *J. of Microbioloaical Methods*, 2005, 60, 207-216.

Bosma, R. et al., "Ultrasound, a new separation technique to harvest microlalgae", *J. Appl. Phycology*, 2003, 15, 143-153.

Bossuyt, X. et al., "Comparative Analysis for Whole Blood Lysis Methods for Flow Cytometry", *Cytometry*, 1997, 30, 124-133.

Brodeur, P. H., "Acoustic Separation in a Laminar Flow," Ultrasonics Symposium, 1994, 1359-1362.

Caperan, P.H. et al., "Acoustic Agglomeration of a Glycol Fog Aerosol: Influence of Particle Concentration and Intensity of the Sound Field at Two Frequencies", *J. Aerosol Sci.*, 1995, 26, 595-612.

Chase, E.S. et al., "Resolution of Dimly Fluorescent Particles: a Practical Measure of Fluorescence Sensitivity", *Cytometry*, 1998, 33, 267-279.

Cheung, et al., "Impedance Spectroscopy Flow Cytometry: On-Chip Label-Free Cell Differentiation," *Cytometry Part A*, Feb. 10, 2005, 65A, 124-132.

Coakley, W.T. et al., "Cell-cell contact and membrane spreading in an ultrasound trap", *Colloids and Surfaces B: Biointerfaces*, 2004, 34, 221-230.

Coakley, W.T. et al., "Ultrasonic separations in analytical biotechnology", *Tibtech*, 1997, 15, 506-511.

Coakley, W.T. et al., "Analytical scale ultrasonic standing wave manipulation of cells and microparticles", *Ultrasonics*, 2000, 38, 638-641.

Condrau, M.A. et al., "Time-Resolved Flow Cytometry for the Measurement of Lanthanide Chelate Fluorescence: I. Concept and Theoretical Evaluation", *Cytometry*, 1994, 16, 187-194.

Condrau, M.A. et al., "Time-Resolved Flow Cytometry for the Measurement of Lanthanide Chelate Fluorescence: II. Instrument Design and Experimental Results", *Cytometry*, 1994, 16, 195-205.

Cousins, C.M. et al., "Plasma Preparation from Whole Blood Using Ultrasound", *Ultrasound in Med. & Biol.*, 2000, 26, 881-888.

Curtis, H.W. et al., "Ultrasonic Continuous Flow Plasmapheresis Separator", *IBM Tech. Disc. Bulletin*, 1982, 25,192-193.

Czyz, H. et al., "On the Concentration of Aerosol Particles by Means of Drift Forces in a Standing Wave Field", *Acustica*, 1990, 70, 23-28.

Dain, Y. et al., "Dynamics of Suspended Particles in a Two-Dimensional High-Frequency Sonic Field", *J. Aerosol Sci.*, 1995, 26, 575-594.

Dain, Y. et al., "Side drift of aerosols in two-dimensional resonant acoustic levitators", *J. Acoust. Soc. Am*, 1997, 102, 2549-2555.

Danilov, S D. et al., "Mean force on a small sphere in a sound field in a viscous fluid", *J. Acoust. Soc. Am.*, 2000, 107, 143-1 53.

Danilov, S.D. et al., "The Mean Force Acting on a Small Body in an Axisymmetric Sound Field in a Real Medium", *Izvestiva Adademii Nauk SSSR, Mekhanika Zhidkosti I Gaza*, 1985, 5, 812-820.

Dean, P.N. et al., "Hydrodynamic Orientation of Sperm Heads for Flow Cytometry", *Biophys. J.*, 1978, 23, 7-13.

(56) References Cited

OTHER PUBLICATIONS

Doblhoff-Dier, 0. et al., "A Novel Ultrasonic Resonance Field Device for the Retention of Animal Cells", *Biotechnol. Prog.*, 1994, 10, 428-432.

Doinikov, A.A. et al., "Acoustic radiation force on a spherical particle in a viscous heat-conducting fluid. I. General formula", *J. Acoust. Soc. Am.*, 1997, 101, 713-721.

Doinikov, A.A. et al., "Acoustic radiation force on a spherical particle in a viscous heat-conducting conducting fluid. II. Force on a rigid sphere", *J. Acoust. Soc. Am.*, 1997, 101, 722-730.

Doinikov, A.A. et al., "Acoustic radiation force on a spherical particle in a viscous heat-conducting fluid. III. Force on a liquid drop", *J. Acoust. Soc. Am.*, 1997, 101, 731-740.

Doinikov, A.A. et al., "Acoustic radiation pressure on a rigid sphere in a viscous fluid", *Proc. R. Soc. Lond.*, 1994, 447-466.

Donnert, G. et al., "Major signal increase in fluorescence microscopy through dark-state relaxation", *Nature Methods*, 2007, 4, 81-86.

Doornbos, R.M. et al., "Experimental and Model Investigations of Bleaching and Saturation of Fluorescence in Flow Cytometry", *Cytometry*, 1997, 29,204-214.

Fenniri, H. et al., "Classification of Spectroscopically Encoded Resins by Raman Mapping and Infrared Hyperspectral Imaging", *Journal of Combinatorial Chemistry*, 2006, 8, 192-198.

Fulwyler, M.J. et al., "Hydronamic Orientation of Cells", *Histochem. Cytoche.*, 1977, 7, 781-783.

Gaida, T.H. et al., "Selective Retention of Viable Cells in Ultrasonic Resonance Field Devices", *Biotech. Prog.*, 1996, 12, 73-76.

Gao, X. et al., "Quantum Dot-Encoded Mesoporous Beads with High Brightness and Uniformity: Rapid Readout Using Flow Cytometry", *Anal. Chem.*, 2004, 3, 2406-2410.

Gherardini, L. et al., "A New Immobilisation Method to Arrange Particles in a Gel Matrix by Ultrasound Standing Waves", *Ultrasound in Med. & Biol.*, 2005, 31, 261-272.

Goddard, G.R. et al., "Ultrasonic Concentration in a Line Driven Cylindrical Tube", *Dissertation*, 2004, 1-276.

Goddard, G. et al., "Single Particle High Resolution Spectral Analysis Flow Cytometry", *Cytometry*, 2006, 69A, 842-851.

Goddard, G. et al., "Ultrasonic particle concentration in a line-driven cylindrical tube", *J. Acoust. Soc. Am.*, 2005, 117, 3440-3447.

Goddard, G. et al., "Ultrasonic Particle-Concentration for Sheathless Focusing of Particles for Analysis in a Flow Cytometer", *Cytometry*, 2006, 69, 66-74.

Gonzalez, I. et al., "Precise Measurements of Particle Entertainment in a Standing-Wave Acoustic Field Between 20 and 3500 Hz", *J. Aerosol Sci.*, 2000, 31,1461-1468.

Gor'Kov, L.P. et al., "On the forces acting on a small particle in an acoustical field in an ideal fluid", *Soviet Physics-Doklady*, 1962, 6, 773-775.

Gould, R.K. et al., "Upper sound pressure limits on particle concentration in fields of ultrasonic standing-wave at megahertz frequencies", *Ultrasonics*, 1992, 30, 239-244.

Gould, R.K. et al., "The effects of acoustic forces on small particles in suspension", *Proceedings of the 1973 Symposium on Finite Amplitude Wave Effects in Fluids*, Bjorno, L., ed., Pergamon, Guildford, 1974, 252-257.

Groschl, "Automatic frequency control for piezoelectric resonators and their implementation in the acoustic driftwave resonator", Thesis implemented at the Institute for General Physics the Technical University of Vienna, Nov. 1991, 2 pages.

Grossner, M.T. et al., "Single fiber model of particle retention in an acoustically driven porous mesh", *Ultrasonics*, 2003, 41, 65-74.

Grossner, M.T. et al., "Single-Collector Experiments and Modeling of Acoustically Aided Mesh Filtration", *Amer. Inst. of Chem. Eng.*, 2005, 51, 1590-1598.

Grossner, M.T. et al., "Transport analysis and model for the performance of an ultrasonically enhanced filtration process", *Chem. Ena. Sci.*, 2005, 60, 3233-3238.

Gupta, S. et al., "Acoustically driven collection of suspended particles within porous media", *Ultrasonics*, 1997, 35, 131-139.

Gupta, S. et al., "Fractionation of Mixed Particulate Solids According to Compressibility Using Ultrasonic Standing Wave Fields", *Chem. Eng. Sci.*, 1995, 50, 3275-3284.

Haake, A. et al., "Contactless micromanipulation of small particles by an ultrasound field excited by a vibrating body", *J. Acoust. Soc. Am.*, 2005, 117, 2752-2760.

Haake, A. et al., "Manipulation of Cells Using an Ultrasonic Pressure Field", *Ultrasound in Med. & Biol.*, 2005, 31, 857-864.

Haake, A. et al., "Positioning of small particles by an ultrasound field excited by surface waves", *Ultrasonics*, 2004, 42, 75-80.

Haake, et al., "Positioning, Displacement, and Localization of Cells Using Ultrasonic Forces," Biotechnology and Bioengineering, 92(1), Aug. 10, 2005, 8-14.

Habbersett, R.C. et al., "An Analytical System Based on a Compact Flow Cytometer for DNA Fragment Sizing and Single Molecule Detection", *Cytometry* 2004, 60A,125-134.

Hager, F. et al., "A Summary of All Forces Acting on Spherical Particles in a Sound Field", *Proc. of the Ultrasonic International '91 Conference and Exhibition*, Le Touauet, France, 1991, 1-4.

Hamilton, M.F. et al., "Acoustic streaming generated by standing waves in two-dimensional channels of arbitrary width", *J. Acoust. Soc. Am.*, 2003, 113, 153-160.

Hamilton, M.F. et al., "Linear and nonlinear frequency shifts in acoustical resonators with varying cross sections", *J. Acoust. Soc. Am.*, 2001, 110, 109-119.

Hancock, A., "Observation of Forces on Microparticles in Acoustic Standing Waves", *Thesis, submitted in partial satisfaction of the reaquirements for the degree of Master of Science in Biomedical Engineering*, University of California, Davis, 2001, 1-155.

Harma, H. et al., "Zeptomole detection sensitivity of prostate-specific antigen in a rapid microtitre plate assay using time-resolved fluorescence", *Luminescence*, 2000, 15, 351-355.

Harris, N.R. et al., "A silicon microfluidic ultrasonic separator", *Sensors and Actuators*, 2004, 95, 425-434.

Harrison, B.S. et al., "Near-Infrared Photo- and Electroluminescence of Alkoxy-Substituted Poly (p-phenylene) and Nonconjugated Polymer/Lanthanide Tetraphenylporphyrin Blends", *Chemistrv of Materials*, 2004, 16, 2938-2947.

Hatanaka, S-I et al., "Effect of Process Parameters on Ultrasonic Separation of Dispersed Particles in Liquid", *Jpn. J. ADPI. Phvs.*, 1999, 38, 3096-3100.

Hawkes, et al., "Continuous Cell Washing and Mixing Driven by an Unltrsound Standing Wave Within a Microfluidic Channel," Lab Chip, 4, Sep. 27, 2004, 446-452.

Hawkes, J.J. et al., "Force field particle filter, combinin ultrasound standing waves and laminar flow", *Sensors and Actuators B*, 2001, 75, 213-222.

Hawkes, J.J. et al., "Microparticle manipulation in millimetre scale ultrasonic standind wave chambers", *Ultrasonics*, 1998, 36, 925-931.

Hawkes, J.J. et al., "Single half-wavelength ultrasonic particle filter: Predictions of the transfer matrix multilayer resonator model and experimental filtration results", *J. Acoust. Soc. Am.*, 2002, 111, 1259-1266.

Hawkes, J.J. et al., "A laminar flow expansion chamber facilitating downstream manipulation of particles concentrated using an ultrasound standing wave", *Ultrasonics*, 1998, 36, 901-903.

Hawkes, J.J. et al., "Ultrasonic deposition of cells on a surface", *Biosensors and Bioelectronics*, 2004, 19,1021-1028.

Hemmila, I. et al., "Progress in Lanthanides as Luminescent Probes", *J. Fluoresnence*, 2005, 15, 529-542.

Hertz, H.M. et al., "Standing-wave acoustic trap for nonintrusive positioning of microparticles", *J. Appl. Phys.*, 1995, 78, 4845-4849.

Higashitani, K.O. et al., "Migration of Suspended Particles in Plane Stationary Ultrasonic Field", *Chem. Eng. Sci.*, 1981, 36, 1187-1192.

Hill M. et al., "Modelling in the design of a flow-through ultrasonic separator", *Ultrasonics*, 2000, 38, 662-665.

Hill M. et al., "Modelling of layered resonators for ultrasonic separation", *Ultrasonics*, 2002, 40, 385-392.

Hill, D.H. et al., "Operating Characteristics of Acoustically Driven Filtration Processes for Particulate Suspensions", *Sep. Sci. and Tech.*, 2000, 35, 1363-1375.

(56) References Cited

OTHER PUBLICATIONS

Hill, M. et al., "The selection of layer thicknesses to control acoustic radiation forces profiles in layered resonators", *J. Acoust. Soc. Am.*, 2003, 114(5), 2654-2661.

Hirschfeld, T. et al., "Fluorescence Background Discrimination by Prebleaching", *J. Histochem. and Cytochem.*, 1979, 27, 96-101.

Holmes, D. et al., "High throughput particle analysis: Combining dielectrophoretic particle focussing with confocal optical detection", *Biosensors and Bioelectronics*, 2006, 21, 1621-1630.

Holwill, I.L. et al., "The use of ultrasonic standing waves to enhance optical particle sizing equipment", *Ultrasonics*, 2000, 38, 650-653.

Huhtinen, P. et al., "Synthesis, Characterization, and Application of Eu(III), Tb(III), Sm (III), and Dy(III) Lanthanide Chelate Nanoparticle Labels", *Anal. Chem.*, 2005, 77, 2643-2648.

Invitrogen, "Fluo-4 NW Calcium Assay Kits (F36205, F36206)", *Product Information*, 2006.

Invitrogen, "Fluorophore selection guide for flow cytometry", *Cellular Analysis*, 2007.

Johnston, P.A. et al., "Cellular platforms for HTS: three case studies", *DDT*, 2002, 7, 353-363.

Jonsson, H. et al., "Particle separation using ultrasound can be used with human shed mediastinal blodd", *Perfusion*, 2005, 20, 39-43.

Juarez, J.A. et al., "Piezoelectric Transducer for Air-Borne Ultrasound", *Acustica*, 1973, 29, 234-239.

Kaduchak, G. et al., "E6 diffraction catastrophe of the primary rainbow of oblate water drops: observations with white-light and laser illumination", *Applied Optics*, 1994, 33, 4691-4696.

Kaduchak, G. et al., "Hyperbolic umbilic and E6 diffraction catastrophes associated with the secondary rainbow of oblate water drops: observations with laser illumination", *Applied Optics*, 1994, 33, 4697-4701.

Kapishnikov, S. et al., "Continuous particle size separation and size sorting using ultrasound in a microchannel", *J. Stat. Mech.*, 2006, 1-13.

Karumanchi, R.S. et al., "Field-assisted extraction of cells, particles and macromolecules", *TRENDS is Biotech*, 2002, 20, 72-78.

Kaye, P.H. et al., "Spatial light-scattering analysis as a means of characterizing and classifying non-spherical particles", *Meas. Sci. Technol.*, 1998, 9, 141-149.

Keij, et al., "Coincidence in High-Speed Flow Cytometry: Models and Measurements," Cytometry 12, Jan. 22, 1991, 398-404.

Kilburn, D.G. et al., "Enhanced Sedimentation of Mammalian Cells following Acoustic Aggregation", *Biotech. and Bioeng.*, 1989, 34, 559-562.

King, L.V. et al., "On the acoustic radiation on spheres", *Proc. R. Soc. A.*, 1933, 147, 212-240.

Kogan, S. et al., "Acoustic concentration of particles in piezoelectric tubes: Theoretical modeling of the effect of cavity shape and symmetry breaking", *J. Acoust. Soc. Am.*, 2004, 116, 1967-1974.

Kozuka, T. et al., "Acoustic Micromanipulation Using a Multi-Electrode Transducer", *7th Inter. Svmp. on Micro Machine and Human Science IEEE*, 1996, 163-170.

Kozuka, T. et al., "Control of a Standing Wave Field Using a Line-Focused Transducer for Two-Dimensional Manipulation of Particles", *Jpn. J. Appl. Phys.*, 1998, 37, 2974-2978.

Kozuka, T. et al., "Micromanipulation Using a Focused Ultrasonic Standing Wave Field", *Electronics and Communications in Japan*, 2000, Part 3, 83(1), 1654-1659.

Kumar, M. et al., "Fractionation of Cell Mixtures Using Acoustic and Laminar Flow Fields", *Biotech. Bioeng.*, 2005, 89, 129-137.

Kundt, A. et al., "Longitudinal vibrations and acoustic figures in cylindrical columns of liquids", *Annalen der Physik and Chemie (Poggendorff's Annalen)*, 1874, 153, 1-12.

Kuznetsova, L.A. et al., "Cavitation buble-driven cell and particle behavior in a ultrasound standing wave", *J. Acoust. Soc. Am.*, 2005, 117, 104-112.

Kuznetsova, L.A. et al., "Microparticle concentration in short path length ultrasonic resonators: Roles of radiation pressure and acoustic streaming", *J. Acoust. Soc. Am.*, 2004, 116, 1956-1966.

Kwiatkowski, C.S. et al., "Resonator frequency shift due to ultrasonically induced microparticle migration in an aqueous suspension: Observations and model for the maximum frequency shift", *J. Acoust. Soc. Am.*, 1998, 103, 3290-3300.

Lakowicz, J.R. et al., "On the Possibility of Long-Wavelength Long-Lifetime High-Quantum-Yield Luminophores", *Analytical Biochemistry*, 2001, 288, 62-75.

Leif, R.C. et al., "Increasing the Luminescence of Lanthanide Complexes", *Cytometry*, 2006, 69A, 767-778.

Leif, R.C. et al., "Markers for Instrumental Evaluation of Cells of the Female Reproductive Tract; Existing and New Markers", in *The Automation of Uterine Cancer Cytology Tutorials of Cytology*, (edited by G.L. Wied. et al.), 1976, 313-344.

Lierke, E.G. et al., "Acoustic Positioning for Space Processing of Materials Science Samples in Mirror Furnaces", *IEEE Ultrasonics Symposium*, 1983, 1129-1139.

Lilliehorn, T. et al., "Trapping of microparticles in the rear field of an ultrasonic transducer", *Ultrasonics*, 2005, 43, 293-303.

Lofstedt, R. et al., "Theory of long wavelength acoustic radiation pressure", *J. Acoust. Soc. Am.*, 1991, 90, 2027-2033.

Loken, M.R. et al., "Cell Discrimination by Multiangle Light Scattering", *Histochem. Cytochem.*, 1976, 24, 284-291.

Loken, M.R. et al., "Identification of Cell Asymmetry and Orientation by Light Scattering", *Histochem. Cytochem.*, 1977, 7, 790-795.

Macey, M.G. et al., "Comparative Study of Five Commercial Reagents for Preparing Normal and Leikaemic Lymphoctyes for Immunophenotypic Analysis by Flow Cytometry", *Cytometry*, 1999, 38, 153-160.

Maltsev, V.P. et al., "Scanning flow cytometry for individual particle analysis", *Review of Scientific Instruments*, 2000, 71, 243-255.

Mandralis, Z. et al., "Enhanced synchronized ultrasonic and flow-field fractionation of suspensions", *Ultrasonics*, 1994, 32, 113-121.

Mandralis, Z. et al., "Transient Response of Fine Particle Suspensions to Mild Planar Ultrasonic Fields", *Fluid/Particle Separation J.*, 1990, 115-121.

Marston, P.L. et al., "Generalized rainbows and unfolded glories of oblate drops: organization for multiple internal reflection and extension of cusps into Alexander's dark band", *Applied Optics*, 1994, 33, 4702-4713.

Marston, P.L. et al., "Manipulation of Fluid Objects with Acoustic Radiation Pressure", *Ann. N.Y. Acad. Sci.*, 2004, 1027, 414-434.

Marston, P.L., "Tensile Strength and Visible Ultrasonic Cavitation of Superfluid 4He*," Journal of Low Temperature Physics, 25(3/4), Mar. 5, 1976, 383-407.

Marston, P.L. et al., "Resonances, Radiation Pressure, and Optical Scattering Phenomena of Drops and Bubbles", *Proceedings of the Second International Colloquium on Drops and Bubbles, Jet Prop. Lab. Pub 82-7* Pasadena, CA, 1982, 166-174.

Martin, K.M. et al., "Acoustic filtration and sedimentation of soot particles", *Experiments in Fluids*, 1997, 23, 483-488.

Masudo, T. et al., "Particle Characterization and Separation by a Coupled Acoustic-Gravity Field", *Analytical Chemistry* 2001, 73, 3467-3471.

Mathies, R.A. et al., "Optimization of High-Sensitivity Fluorescence Detection", *Anal. Chem.*, 1990, 62, 1786-1791.

Mazumdar, M.K. et al., "Spart Analyzer: Its Application to Aerodynamic Size Distribution Measurement", *J. Aerosol Sci.*, 1979, 10, 561-569.

Mazumdar, M.K. et al., "Single particle aerodynamic relaxation time analyzer", *Rev. Sci. Instrum.*, 1977, 48, 622-624.

McCartin, B.J., "A Numerical Procedure for 2D Acoustic Waveguides with Heated Walls", http://flux.aps.org/meetings/YR99/OSS99/abs/S700004.html, 1999.

Meindersma, G.W. et al., "Separation of a biocatalyst with ultrafiltration or filtration after bioconversion", *J. Membrane Sci.*, 1997, 125, 333-349.

Morgan, J. et al., "Manipulation of in vitro toxicant sensors in an ultrasonic standing wave", *Toxicology in Vitro*, 2004, 18, 115-120.

Mullaney, P.F. et al., "The Small Angle Light Scattering of Biological Cells", *Biophys. J.*, 1970, 10, 764-772.

Neild, A., "A micro-particle positioning technique combining an ultrasound manipulator and a microgripper," *J. Micromechanical Microengineering*, 2006, 16, 1562-1570.

(56) References Cited

OTHER PUBLICATIONS

Neild, A. et al., "Design, modeling and characterization of microfluidic devices for ultrasonic manipulation", *Sensors and Actuators B: Chemical*, Feb. 20, 2007, 121(2).

Neukammer, J. et al., "Angular distribution of light scattered by single biological cells and oriented particle agglomerates", *Appl. Opt.*, 2003, 42, 6388-6397.

Nilsson, A. et al., "Acoustic control of suspended particles in micro fluidic chips", *Lab Chip*, 2004, 4, 131-135.

Nolan et al., "Suspension Array Technology: New Tools fro Gene and Protein Analysis", *Cell and Molecular Biology*, 2001, 47, 1241-1256.

Nowotny, H. et al., "Layered piezoelectric resonators with an arbitrary No. electrodes (general one-dimensional treatment)", *J. Acoust. Soc. Am.*, 1991, 90, 1238-1245.

Otaki, M. et al., "Virus Removal in a Membrane Separation Process", *Water Sci. and Tech.*, 1998 37, 107-116.

Pangu, G.D. et al., "Acoustically aided separation of oil droplets from aqueous emulsions", *Chem. Eng. Sci.*, 2004, 59, 3183-3193.

Petersson et al., "Separation of Lipids from Blood Utilizing Ultrasonic Standing Waves in Microfluidic Channels," *Analyst*, 2004, 129, 938-943.

Petersson, F., "Particle Flow Switch Utilizing Ultrasonic Particle Switching in Microfluidic Channels", *7th International Conf on Miniaturizing Chem and Biochem Analysis Systems*, 2003, 879-882.

Petersson, F. et al., "Continuous separation of lipid particles from erythrocytes by means of laminar flow and acoustic standing wave forces", *Lab Chip*, 2005, 5, 20-22.

Petersson, F. et al., "Carrier Medium Exchange through Ultrasonic Particle Switching in Microfluidic Channels", *Anal. Chem.*, 2005, 77, 1216-1221.

Petersson, F. et al., "Free Flow Acoustophoresis: Microfluidic-Based Mode of Particle and Cell Separation", *Anal. Chem.*, 2007 79, 5117-5123.

Pregibon, D.C. et al., "Multifunctional Encoded Particles for High-Throughput Biomolecule Analysis", *Science*, 2007, 315, 1393-1396.

Princen, K. et al., "Evaluation of SDF-1/CXCR4-Induced Ca2+Signaling by Fluorometric Imaging Plate Reader (FLIPR) and Flow Cytometry", *Cytometry*, 2003, 51A, 35-45.

Pui, P.W. et al., "Batch and Semicontinuous Aggregattion and Sedimentation of Hybridoma Cells by Acoustic Resonance Fields", *Biotechnol. Prog.*, 1995, 11, 146-152.

Rama Rao, G.V. et al., "Monodisperse Mesoporous Silica Microspheres Formed by Evaporation-Induced Self Assembly of Surfacant Templates in Aerosols", *Advanced Materials*, 2002, 18,1301-1304.

Rens, W. et al., "A Novel Nouel for More Efficient Sperm Orientation to Improve Sorting Efficiency of X and Y Chromosome-Bearing Sperm", *Cytometry*, 1998, 33, 476-481.

Ricks, D.C. et al., "A numerically stable global matrix method for cylindrically layered shells excited by ring forces", *J. Acoust. Soc. Am.*, 1994, 95, 3339-3349.

Rouleau, F. et al., "Electromagnetic scattering by compact clusters of spheres", *Astron. Astrophys*, 1996, 310, 686-698.

Rudnick, J., "Oscillational instabilities in single-mode acoustic levitators", *J. Acoust. Soc. Am.*, 1990, 87, 81-92.

Saito, M. et al., "Microorganism manipulation and microparticle arrangement by the use of ultrasonic standing waves", *SPIE*, 2001, 4590, 26-37.

Saito, M. et al., "Ultrasonic manipulation of locomotive microorganisms and evaluation of their activity", *J. App. Phvsics*, 2002, 92, 7581-7586.

Saito, M. et al., "Ultrasonic trapping of paramecia and estimation of their locomotive force", *Appl. Phys. Lett*,1997, 71,1909-1911.

Saito, M. et al., "Ultrasonic waves for fabricating lattice structure in composite materials", *SPIE*, 1999, 3786, 179-190.

Saito, M. et al., "Quantum mechanical representation of acoustic streaming and acoustic radiation pressure", *Physical Review*, 2001, E64, 026311-1-026311-5.

Samiotaki, M. et al., "Seven-Color Time-Resolved Fluorescence Hybridization Analysis of Human Papilloma Virus Types", *Analytical Biochem.*, 1997, 253, 156-161.

Schmid, M. et al., "A computer-controlled system for the measurement of complete admittance spectra of piezoelectric resonators", *Meas. Sci. Technol.*, 1990, 1, 970-975.

Schoell, W.M. et al., "Separation of Sperm and Vaginal Cells with Flow Cytometry for DNA Typing After Sexual Assault", *Obstetrics and Gynecolony*, 1999, 94, 623-627.

Semianov, K.A. et al., "Measurement of Mammalian Erythrocyte Indices from Light Scattering with Scaning Flow Cytometer", *Proc. SPIE*, 2003, 5141,106-113.

Sethu, P. et al., "Continuous Flow Microfluidic Device for Rapid Erythrocyte Lysis", *Anal. Chem.*, 2004, 76, 6247-6253.

Shapiro, H.M. et al., *Practical Flow Cytometry*, Hoboken, NJ, John Wiley & Sons. Inc., 2005, 9-13.

Shvalov, A.N. et al., "Individual *Escherichia coli* Cells Studied from Light Scattering with the Scanning Flow Cytometer", *Cytometry*, 2000, 41, 41-45.

Shvalov, A.N. et al., "Light -scattering properties of individual erythrocytes", *Applied Optics*, 1999, 38, 230-235.

Simpson, H.J. et al., "Ultrasonic four-wave mixing mediated by an aqueous suspension of microspheres: Theoretical steady-state properties", *J. Acoust. Soc. Am.*, 1995, 98, 1731-1741.

Skudrzyk, E. et al., "Die Grundlagen der Akustic", *Sprinaer Verlaa. Wien*, 1954, 202-205 and 807-825.

Slomkowski, S. et al., "New Types of Microspheres and Microsphere-related Materials for Medical Diagnostics", *Polymers for Advanced Technologies*, 2002, 13, 906-918.

Sobanski, M.A. et al., "Sub-micron particle manipulation in an ultrasonic standing wave: Applications in detection of clinically important biomolecules", *Bioseparation*, 2001, 9, 351-357.

Steinkamp, J.A., "A Differential Amplifier Circuit for Reducing Noise in Axial Light Loss Measurements", *Cyometry*, 1983, 4, 83-87.

Steinkamp, J.A. et al., "Dual-Laser, Differential Fluorescence Correction Method for Reducing Cellular Background Autofluorescence", *Cytometry*,1986, 7, 566-574.

Steinkamp, J.A. et al., "Enhanced Immunofluorescence Measurement Resolution of Surface Antigens on Highly Autofluorescent, Glutaraldehyde-Fixed Cells Analyzed by Phase-Sensitive Flow Cytometry", *Cytometry*, 1999, 37, 275-283.

Stewart, C.C. et al., "Resolving Leukocytes Using Axial Light Loss", *Cytometry*, 1989, 10, 426-432.

Stoffel, C.L. et al., "Data Analysis for a Dual Analysis for a Dual-Channel Virus Counter", *Analytical Chemistry*, 2005, 77, 2243-2246.

Stoffel, C.L. et al., "Design and Characterization of a Compact Dual Channel Virus Counter", *Cytometry*, 2005, Part A 65A, 140-147.

Stovel, R.T. et al., "A Means for Orienting Flat Cells in Flow Systems", *Biophys J.*, 1978, 23, 1-5.

Takeuchi, M. et al., "Ultrasonic Micromanipulation of Small Particles in Liquid", *Jpn J. Appl. Phys.*, 1994, 33, 3045-3047.

Takeuchi, J. et al., "Ultrasonic Micromanipulator Using Visual Feedback", *Jpn J. Appl. Phys.*, 1996, 35, 3244-3247.

Thiessen, D.B. et al., "Principles of some Acoustical, Electrical, and Optical Manipulation Methods with Applications to Drops, Bubbles, and Capillary Bridges", *ASME Fluids Eng. Div. Publ. FED*, 1998.

Thiessen, D.B. et al., "Some Responses of Small Diffusion Flames to Ultrasonic Radiation", *NASA*, 2003, 321-324.

Tolt, T.L. et al., "Separation devices based on forced coincidence response of fluid-filled pipes", *J. Acoust. Soc. Am.*, 1992, 91, 3152-3156.

Tolt, T.L. et al., "Separation of Dispersed Phases from Liquids in Acoustically Driven Chambers", *Chem. Eng. Science*, 1993, 48, 527-540.

Townsend, R.J. et al., "Modelling of particle paths passing through an ultrasonic standing wave", *Ultrasonics*, 2004, 42, 319-324.

Trihn, E.H. et al., "Experimental study of streaming flows associated with ultrasonic levitators", *Phys. Fluids*, 1994, 6, 3567-3579.

Trinh, E.H. et al., "Compact acoustic levitation device for studies in fluid dynamics and material science in the laboratory and microgravity", *Rev. Sci. Instrum.*, 1985, 56, 2059-2065.

Tuckermann, R. et al., "Trapping of heavy gases in stationary ultrasonic fields", *Chem. Phys. Ltrs.*, 2002, 363, 349-354.

(56) References Cited

OTHER PUBLICATIONS

Tung, Yi-C. et al., "PDMS-based opto-fluidic micro flow cytometer with two-color, multi-angle fluorescence detection capability using PIN photodiodes", *Sensors and Actuators*, 2004, 98, 356-367.
Tyson, D.S. et al., "Ruthenium (II) complex with a notably long excited state lifetime", *The Royal Society of Chemistry*, 2000, 2355-2356.
Vainshtein, P. et al., "On the Drift of Aerosol Particles in Sonic Fields", *J. Aerosol Sci.*, 1992, 23, 631-637.
Vainshtein, P. et al., "The effect of centreline particle concentration in a wave tube", *J. Fluid Mech.*, 1996, 306, 31-42.
Van Hee, P. et al., "Strategy for Selection of Methods for Separation of Bioparticles From Particle Mixtures", *Biotech. Bioeng.*, 2006, 94, 689-709.
Verpoorte, E. et al., "Beads and chips: new recipes for analysis—Elisabeth Verpoorte reviews particle handling in microchannels", *Lab Chip*, 2003, 3, 60N-68N.
Visuri, S.V. et al., "Microfluidic tolls for biological sample preparation", *Poster 1423, 2nd Annual International IEEE-EMBS Special Topic Cofnerence on Microtechnologies in Medicine & Biology*, May 2-24, 2002, 556-559.
Wang, Z. et al., "Retention and Viability Characteristics of Mammalian Cells in an Acoustically Driven Polymer Mesh", *Biotechnol. Prog.*, 2004, 20, 384-387.
Ward, M. et al., "Manipulation of Immunomagnetic Targets in Microfluidic Channel Flow", *Dissertation*, 2005, 1-205.
Weiser, M.A. et al., "Interparticle Forces on Red Cells in a Standing Wave Field", *Acustica*, 1984, 56, 114-119.
Weiser, M.A.H. et al., "Extension of acoustic levitation to include the study of micron-size particles in a more compressible host liquid", *J. Acoust. Soc. Am.*, 1982, 71, 1261-1268.
Whitworth, G. et al., "Particle column formation in a stationary ultrasonic field", *J. Acoust. Soc. Am.*, 1992, 91, 79-85.
Whitworth, G. et al., "Transport and harvesting of suspended particles using modulated ultrasound", *Ultrasonics*, 1991, 29, 439-444.
Wu, Y. et al., "Diazo Coupling Method for Covalent Attachment of Proteins to Solid Substrates", *Bioconjugate Chem.*, 2006, 17, 359-365.
Yagi, et al., "Flow Cytometry to Evaluate Theileria Sergenti Parasitemia Using the Florescent Nucleic Acid Stain SYTO16," *Cytometry*, 2000, 41, 223-225.
Yamakoshi, Y. et al., "Micro particle trapping by opposite phases ultrasonic travelling waves", *Ultrasonics*, 1998, 36, 873-878.
Yasuda, K. et al., "Concentration and Fractionation of Small Particles in Liquid by Ultrasound", *Jpn J. Appl. Phys.*, 1995, 34, 2715-2720.
Yasuda, K. et al., "Deoxyribonucleic acid concentration using acoustic radiation force", *J. Acoust. Soc. Am.*, 1996, 99, 1248-1251.
Yasuda, K. et al., "Non-destructive, non-contact handling method for biomaterials in micro-chamber by ultrasound", *Sensors and Actuators*, 2000, 64, 128-135.
Yasuda, K. et al., "Particle separation using acoustic radiation force and elecrostatic force", *J. Acoust. Soc. Am.*, 1996, 99, 1965-1970.
Yasuda, K. et al., "Blood Concentration by Superposition of Higher Harmonics of Ultrasound", *Jpn. J. Appl. Phys.*, 1997, 36, 3130-3135.
Yasuda, K. et al., "Using acousitc radiation force as a concentration method for erythrocytes", *J. Acoust. Soc. Am.*, 1997, 102, 642-645.
Ye, C-H. et at., "Preparation of three terbium complexes with paminobenzoic acid and investigation of crystal structure influence on luminescence property", *Journal of Solid State Chemistry*, 2004, 177, 3735-3742.
Yosioka, K. et al., "Acoustic Radiation Pressure on a Comressible Sphere", *Acustica*, 1955, 5, 167-173.
Yuan, J. et al. "Lanthanide-based luminescence probes and time-resolved luminescence bioassays", *Trends in Analytical Chemistry*, 2006, 25, 490-500.
Yurkin, M.A. et al., "Experimental and theoretical study of light scattering by individual mature red blook cells by use of scanning flow cytometry and a discrete dipole approximation", *Applied Optics*, 2005, 44, 5249-5256.

EPO Application No. EP 08733084: Extended European Search Report dated Mar. 24, 2010.
Response to Mar. 24, 2010 Extended European Search Report in European Application No. 08733084.1 filed Jun. 16, 2010.
International Application No. PCT/US05/26524: International Search Report dated Oct. 3, 2006.
International Application No. PCT/US08/87579: International Search Report dated Feb. 9, 2009.
International Application No. PCT/US08/87579, Written Opinion dated Feb. 9, 2009.
International Application No. PCT/US2008/059181: International Search Report dated Jul. 25, 2008.
International Application No. PCT/US2009/031154: International Search Report dated Jul. 8, 2009.
U.S. Appl. No. 11/982,042: Restriction Requirement dated Nov. 30, 2009.
U.S. Appl. No. 11/982,042: Non-Final Office Action dated Jun. 10, 2010.
U.S. Appl. No. 11/982,042: Final Office Action dated Sep. 24, 2010.
U.S. Appl. No. 11/982,042: Non-Final Office Action dated Mar. 4, 2011.
U.S. Appl. No. 11/982,042: Final Office Action dated Oct. 17, 2011.
U.S. Appl. No. 12/903,042: Non-Final Office Action dated May 11, 2012.
U.S. Appl. No. 12/903,042: Non-Final Office Action dated Nov. 15, 2012.
U.S. Appl. No. 12/903,042: Final Office Action dated May 24, 2013.
U.S. Appl. No. 11/593,312: Non-Final Office Action dated Oct. 16, 2008.
U.S. Appl. No. 11/593,312: Final Office Action dated May 13, 2009.
U.S. Appl. No. 11/593,312: Non-Final Office Action dated Oct. 23, 2009.
U.S. Appl. No. 11/593,312: Final Rejection dated Apr. 5, 2010.
U.S. Appl. No. 11/593,312: Notice of Allowance dated Jul. 6, 2010.
U.S. Appl. No. 11/593,312: Notice of Allowance dated Sep. 16, 2010.
U.S. Appl. No. 11/784,928: Restriction Requirement dated Jul. 1, 2009.
U.S. Appl. No. 11/784,928: Non-Final Office Action dated Dec. 30, 2009.
U.S. Appl. No. 11/784,928: Final Rejection dated Jul. 7, 2010.
U.S. Appl. No. 11/784,928: Notice of Allowance dated Dec. 13, 2010.
U.S. Appl. No. 11/784,936: Non-Final Office Action dated Apr. 3, 2008.
U.S. Appl. No. 11/784,936: Final Office Action dated Dec. 31, 2008.
U.S. Appl. No. 11/784,936: Non-Final Office Action dated Jun. 24, 2009.
U.S. Appl. No. 11/784,936: Notice of Allowance dated Feb. 22, 2010.
U.S. Appl. No. 11/784,936: Notice of Allowance dated May 28, 2010.
U.S. Appl. No. 11/784,936: Notice of Allowance dated Sep. 16, 2010.
U.S. Appl. No. 12/903,003: Non-Final Office Action dated Nov. 15, 2010.
U.S. Appl. No. 12/903,003: Final Office Action dated Jun. 23, 2011.
U.S. Appl. No. 12/903,003: Non-Final Office Action dated Oct. 24, 2011.
U.S. Appl. No. 12/903,003: Final Office Action dated Feb. 6, 2012.
U.S. Appl. No. 12/903,003: Non-Final Office Action dated Jun. 19, 2012.
U.S. Appl. No. 12/903,003: Final Office Action dated Oct. 24, 2012.
U.S. Appl. No. 12/903,003: Non-Final Office Action dated Feb. 13, 2013.
U.S. Appl. No. 12/903,003: Notice of Allowance dated Jun. 5, 2013.
U.S. Appl. No. 12/283,491: Restriction Requirement dated Jun. 25, 2010.
U.S. Appl. No. 12/283,491: Non-Final Office Action dated Sep. 27, 2010.
U.S. Appl. No. 12/283,491: Final Office Action dated Apr. 5, 2011.
U.S. Appl. No. 12/283,491: Non-Final Office Action dated Sep. 27, 2011.
U.S. Appl. No. 12/283,491: Ex parte Quayle Action dated Mar. 29, 2012.
U.S. Appl. No. 12/283,491: Notice of Allowance dated May 25, 2012.

(56) References Cited

OTHER PUBLICATIONS

U.S. Appl. No. 12/283,461: Restriction Requirement dated Jun. 28, 2010.
U.S. Appl. No. 12/283,461: Non-Final Office Action dated Sep. 28, 2010.
U.S. Appl. No. 12/283,461: Final Office Action dated Apr. 5, 2011.
U.S. Appl. No. 12/283,461: Non-Final Office Action dated Sep. 26, 2011.
U.S. Appl. No. 12/283,461: Ex parte Quayle Action dated Mar. 29, 2012.
U.S. Appl. No. 12/283,461: Notice of Allowance dated May 31, 2012.
U.S. Appl. No. 13/295,934: Non-Final Office Action dated Oct. 9, 2012.
U.S. Appl. No. 13/295,934: Non-Final Office Action dated May 24, 2013.
U.S. Appl. No. 12/903,042: Non-Final Office Action dated Sep. 18, 2013.
U.S. Appl. No. 11/982,042: Non-Final Office Action dated Oct. 22, 2013.
U.S. Appl. No. 13/966,624: Non-Final Office Action dated Sep. 24, 2013.
U.S. Appl. No. 13/966,624: Notice of Allowance dated Feb. 21, 2014, 34 pages.
U.S. Appl. No. 13/571,629: Restriction Requirement dated Dec. 6, 2013, 10 pages.
U.S. Appl. No. 13/966,624: Final Office Action dated Jan. 28, 2014, 15 pages.

* cited by examiner

US 9,074,979 B2

ULTRASONIC ANALYTE CONCENTRATION AND APPLICATION IN FLOW CYTOMETRY

RELATED APPLICATIONS

This application is a continuation of U.S. application Ser. No. 11/982,042, "Ultrasonic Analyte Concentration And Application In Flow Cytometry," filed Oct. 31, 2007. That application is a continuation of U.S. application Ser. No. 10/979,065, "Ultrasonic Analyte Concentration And Application In Flow Cytometry," filed Nov. 2, 2004 (and issued as U.S. Pat. No. 7,340,957 on Mar. 11, 2008), which application claims priority to U.S. application 60/592,169, "Ultrasonic Analyte Concentration And Application In Flow Cytometry," filed Jul. 29, 2004. All of the foregoing applications are incorporated herein by their entireties for any and all purposes.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to the use of ultrasonic energy, and, more particularly, to the use of ultrasonic energy to concentrate analytes within a fluid.

BACKGROUND OF THE INVENTION

The term "analyte" is used throughout the body of this text and is defined as a particle that is of interest to the user of the present invention. The term "particle" is defined as a very small unit of matter, to include but not limited to: biological cells, cell organelles, organic/ inorganic molecules, and microspheres.

The use of acoustic standing waves to concentrate homogeneously suspended particles in a fluid at acoustic pressure nodal or antinodal planes within the fluid was first described by A. Kundt, and O. Lehmann, "Longitudinal vibrations and acoustic figures in cylindrical columns of liquids", *Annalen der Physik and Chemie (Poggendorffs Annalen)*, 153,1-11 (1874). However, the inclusion of suspended particles was used only to enhance the visualization of the ultrasonic waves Kundt and Lehmann sought to describe.

Acoustic forces may be used to non-invasively position, concentrate, or fractionate particles in a fluid. Particles suspended within a fluid filled cavity subject to ultrasonic irradiation experience a time-averaged drift force that transports them to a minima in the acoustic radiation force potential that is dependent upon the acoustic contrast ratio between the particles and the surrounding fluid. For plane waves, positions that correspond to minima in of the acoustic radiation force potential are the pressure nodal and antinodal planes Other forces are also present in a sound wave that exerts torque on particles, which induces spin or alignment of the particles. Secondary forces between particles, due to scattering of the sound field by neighboring particles, also serves to aggregate particles into concentrated clumps.

Microfluidic devices that incorporate the use of acoustic standing waves may be used to filter particles from samples prior to analysis, or separate and position particles within defined flow channels. Acoustic concentration of biological cells can be incorporated in a fully automated analysis system providing contamination-free high-speed, real-time measurements.

The present invention is an apparatus and method for using acoustic force to position, concentrate, or fractionate particles suspended in a fluid. One embodiment of the present invention uses a low-order coupled structure/cavity mode of a long cylindrical fluid-filled glass tube driven by a piezo-ceramic transducer to create a resonant pressure field that is dipole in character within the fluid-filled cavity. Thus, particles within the fluid are driven towards minima in the radiation force potential created by the resonant ultrasonic field. The cylindrical geometry eliminates the need for accurate alignment of a transducer/ reflector system, in contrast to the case where planar, confocal, or traveling wave fields are used. An added benefit of the cylindrical geometry is a lower energy density in the cavity, brought about through excitation of the whole cylinder that results in reduced cavitation, convection, and thermal gradients within the fluid.

U.S. Pat. No. 6,090,295, "Method and Apparatus for Acoustically Demixing Aqueous Solutions", issued on Jul. 18, 2000, by Raghavarao, et al., teaches the use of acoustic energy to demix an aqueous solution that consists of at least two aqueous phases. Here, large amounts of acoustic energy (4-6 Watts/$cm^5$ at 1.2-1.8 MHz) are transmitted from a transducer into an aqueous solution to demix. This differs from the present invention as no resonance modes are utilized to create nodal positions within the aqueous solution and the energy range is such that it would destroy sensitive particles, such as cell structures.

U.S. Pat. No. 5,711,888, "Multilayered Piezoelectric Resonator for The Separation of Suspended Particles", issued on Jan. 27, 1998, by Trampler et al., teaches a method of separating particles suspended within a fluid using acoustic energy. However, the present invention differs in that the cavity is not rectangular, as is taught in Trampler et al., which requires accurate alignment of the system, but instead uses the cylindrically symmetric acoustic modes of the coupled system consisting of the structure and cavity to set up the sought-after resonance and corresponding minima in the acoustic radiation force potential.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes an apparatus and corresponding method for concentrating analytes within a fluid flowing through a tube using acoustic radiation pressure. The apparatus includes a function generator that outputs a radio frequency electrical signal to a transducer that transforms the radio frequency electric signal to an acoustic signal and couples the acoustic signal to the tube. The acoustic signal is converted within the tube to acoustic pressure that concentrates the analytes within the fluid.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1A:
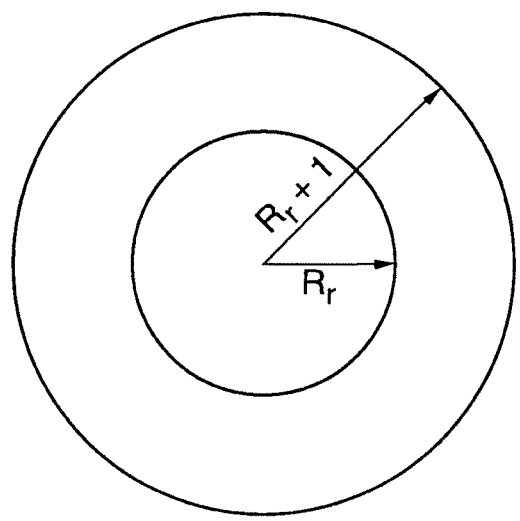
FIGS. 1a and 1b show a cross-section of a cylindrically layered system.

The present invention is an apparatus and method for using acoustic radiation pressure to position, concentrate, or fractionate analytes suspended in a fluid. The natural resonance frequency of a tube is used to concentrate given analytes on the axial center of the tube. A transducer that is attached to the tube provides the acoustic energy. In another embodiment, an additional transducer may also be used for electronic feedback to maintain resonant frequency and for automatic temperature compensation.

Theory

In the first quantitative analysis of the radiation force on a particle in a sound field, King, L. V., "On the acoustic radiation on spheres," *Proc. R. Soc. A.*, 147, 212-240, (1933), considered the acoustic radiation force only. King assumed incompressible spheres, noting that the radiation force on particles with radii less than a wavelength was greater in a standing than a traveling wave field.

L. P. Gorkov, "On the forces acting on a small particle in an acoustical field in and ideal fluid", *Soviet Physics-Doklady*, 6, 773-775 (1962), extended King's analysis to include the influence of particle compressibility on the force moving the particles to nodal or anti-nodal positions.

R. K. Gould, W. T. Coakley, "The effects of acoustic forces on small particles in suspension", in *Proceedings of the 1973 Symposium on Finite Amplitude Wave Effects in Fluids*, edited by L. Bjorno, Pergamon, Guildford, 1974, pp. 252-257, further extended King's analysis to include buoyancy, and acoustic streaming.

Lastly, K. Higashitani, M. Fukushima, Y, Matsuno, "Migration of suspended particles in plane stationary ultrasonic field", *Chem. Eng. Sci.* 36, 1187-1192 (1981), developed terms to account for diffusion of small particles. Following the findings of these authors a quantitative understanding of particle movement in an ultrasonic field was obtained.

For a dilute suspension in an arbitrary field, Gorkov's theory for non-interacting particles provides a good description of the equilibrium particle distribution. The time-averaged potential acting on a small spherical particle of radius r and density $\rho_p$ in a fluid of density $\rho_f$ in an acoustic field is defined as:

$$U = 2\pi r^3 \left[ \frac{\overline{p_{in}^2}}{3\rho_f c_f^2} \frac{c_p^2 \rho_p - c_f^2 \rho_f}{c_p^2 \rho_p} - \rho_f \overline{v_{in}^2} \frac{(\rho_p - \rho_f)}{2\rho_p + \rho_f} \right] \quad (1)$$

where $c_f$ and $c_p$ are the acoustic velocities in the fluid and the given particle respectively, $p_{in}$ and $v_{in}$ are the mean-square fluctuations of the pressure and velocity in the wave at the point where the particle is located. In the case of a plane wave, depending on the relationships between the density and acoustic velocity of the given particle and fluid, the given particle will tend to move either to a pressure anti-node or a pressure node. The velocity and pressure of the acoustic field can be derived utilizing methods such as the global matrix method described below.

Referring now to FIG. 1a, a cylindrically layered system can be modeled using the direct global matrix approach taught by D. C. Ricks, H. Schmidt, "A numerically stable global matrix method for cylindrically layered shells excited by ring forces," *J. Acoust. Soc. Am.* 95, 3339-3349 (1994). The layers of material are numbered n=1 to N where layer 1 includes r=0 and layer N extends to infinity. The variable $r_n$ corresponds to the boundary between layer n and n+1. All layers are assumed to be isotropic and homogeneous viscoelastic with Lame constants $\lambda_n$ and $\mu_n$ and density $\rho_n$. The subscript refers to the layer number described by the constants. If the layer is a solid then the displacement field $u_n$ is governed by the following 3-D equations of elastodynamics:

$$(\lambda n + 2 \cdot \mu n) \nabla \nabla \cdot \vec{u}_n - \mu n \nabla \times \nabla \times \vec{u}_n + f_n = \rho_n \ddot{\vec{u}}_n \quad (2)$$

The variable $f_n$ refers to the applied force per unit volume in layer n. The longitudinal and shear wave speeds in layer n are related to the Lame coefficients as described by:

$$cln = \sqrt{(\lambda n + 2\mu n)/\rho n}, \quad (3)$$

$$csn = \sqrt{\mu n / \rho n} \quad (4)$$

The corresponding wave numbers $h_n$ and $k_n$, the longitudinal and shear wave numbers, respectively, are expressed in terms of the angular frequency $\omega$ and the sound speeds. Here $C_{ln}$ is the longitudinal wave speed in a given elastic material, and $C_{sn}$ is the shear wave speed in a given elastic material:

$$h_n = \omega / c_{ln}, \quad (5)$$

$$k_n = \omega / c_{sn} \quad (6)$$

In fluids, any terms involving $c_{sn}$ and $k_n$ are ignored, as there are no shear forces within a fluid, and $\mu_n=0$. A time dependent ring force of $e^{-i\omega t}$ can be assumed without loss of generality as a time harmonic field of frequency ($\omega$) can be written as an infinite sum of harmonic functions (Fourier Series). Therefore, the time dependence of other forcing functions, including a point or line excitation, can be synthesized from time-harmonic forces by using a Fourier integral over frequency. Similarly angular dependence of $e^{i\nu\Theta}$ is assumed, where $\nu$ is the order. The displacement field can be expressed as the linear superposition of homogeneous and particular solutions. The homogeneous solutions are source-free waves that would emanate from the ring forces in layer n if the layer extended over all space which, when added to the particular solutions, satisfy the boundary conditions. Therefore, the homogeneous field is governed by:

$$(\lambda_n + 2\cdot\mu_n)\nabla\nabla\cdot\vec{u}_n^H - \mu_n\nabla\times\nabla\times\vec{u}_n^H + \rho_n\omega^2\vec{u}_n^H = 0 \quad (8)$$

The field can be expressed in terms of scalar displacement potentials that satisfy the Helmholtz equations. The problem may be further reduced to radial and azimuthal coordinates Although any two of the Bessel and Hankel functions would satisfy the resulting differential equations, numerical stability dictates that the solutions be represented in terms of the Bessel and Hankel function of the first form $H^{(1)}_\nu$. The coefficients are determined using the boundary conditions for each layer. The global matrix is constructed using the unknown displacements and stresses associated with the homogeneous waves, written in terms of an amplitude vector and set equal to the displacements and stresses due to the particular solutions due to the forcing excitation. Solutions for the coefficients are determined by applying Cramer's rule to the global matrix.

Figure 1B:
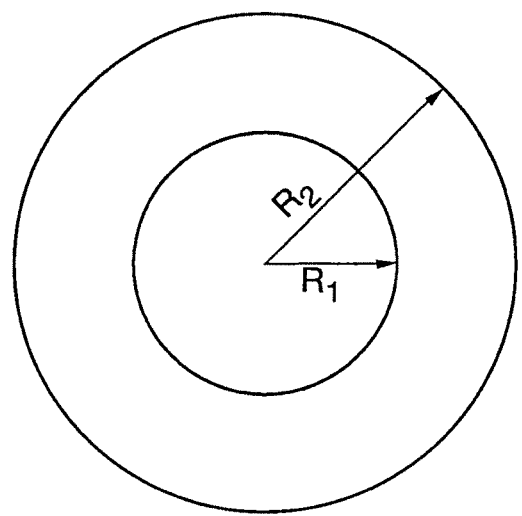

Referring now to FIG. 1b, the boundary conditions, which generate the global matrix, are:

$$\vec{u}_{r1}^H(R1) = \vec{u}_{r2}^H(R1), \quad (9)$$

$$\vec{\sigma}_{rr1}^H(R1) = \vec{\sigma}_{rr2}^H(R1), \quad (10)$$

$$\vec{\sigma}_{r\theta2}^H(R1) = 0, \quad (11)$$

$$\vec{\sigma}_{rr2}^H(R2) = \vec{\sigma}_{rr}^P(R2), \text{ and} \quad (12)$$

$$\vec{\sigma}_{r\theta2}^H(R2) = \vec{\sigma}_{r\theta}^P(R2). \quad (13)$$

The variables R1 and R2 are the internal and external tube radii respectively. The boundary conditions require continuity of displacement at the inner boundary R1. The radial stress is continuous at R1. Since the cylinder is fluid filled, no shear stress is present at the fluid-solid interface at R1. Since the system is being driven at the outer surface, radial and angular stresses are continuous and equal to the particular solutions at the outer boundary R2.

The finite width of the element was accounted for in the calculations by applying a Gaussian weighting function about the point $\theta=3\pi/2$ radians to the forcing function of the particular solutions.

Thus, the boundary value problem presented above is numerically solved to describe the motion of a line driven tube. The results are used to predict the vibrational behavior of outer boundary of the tube and the cavity within the tube. This in turn is used to describe the ability of the tube to concentrate particles and predict the necessary motions for efficient concentration

EXAMPLE 1

Figure 2:
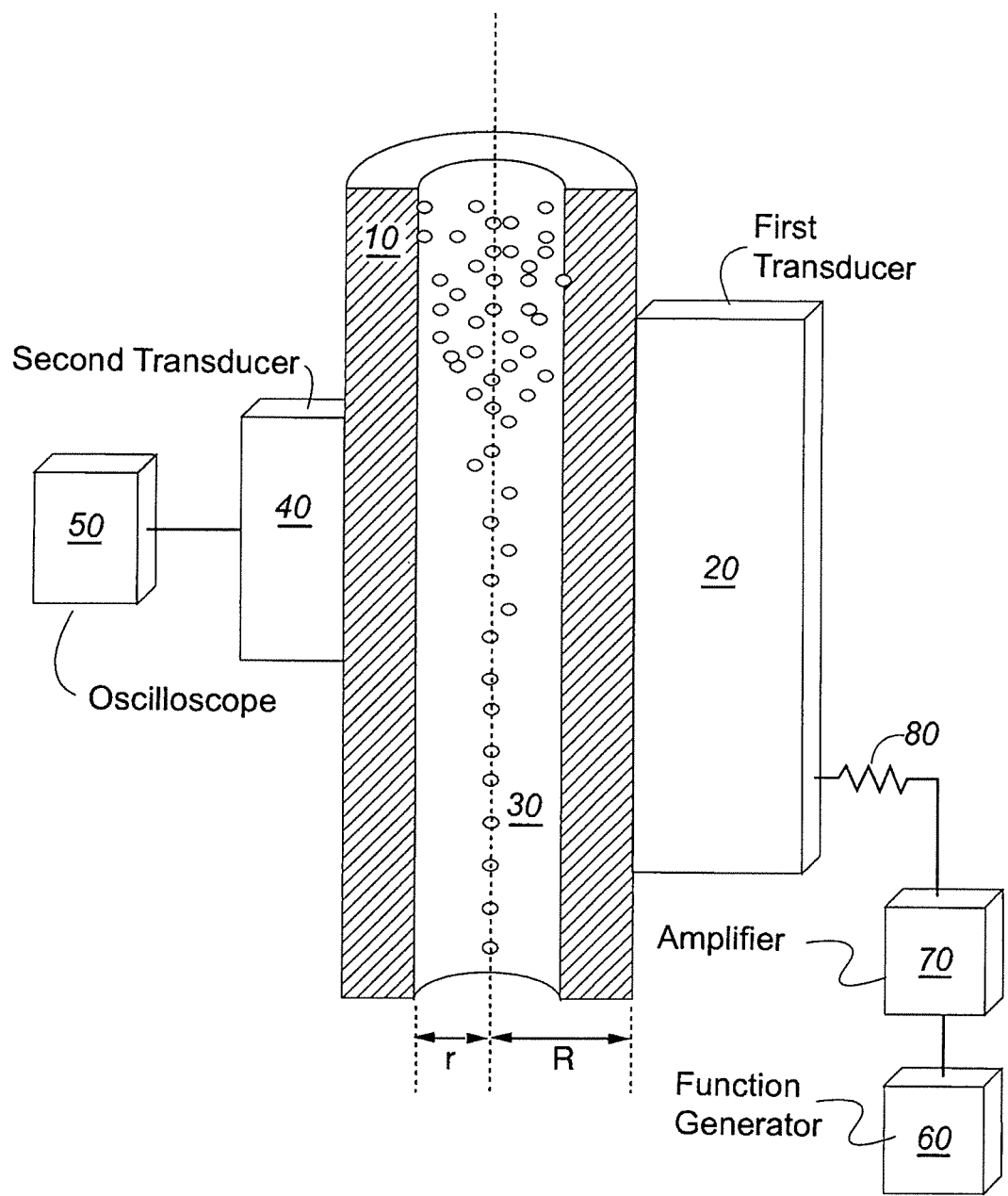
FIG. 2 pictorially illustrates an experimental setup using a glass tube for practicing the present invention.

Referring now to FIG. 2, first transducer 20 was connectively attached, axially to cylindrical glass tube 10 with inner diameter r of 2.2 mm, and outer diameter R of 3.97 mm. In preferred embodiments, materials used for tube 10 include glasses, plastics, metals, or crystalline solids. Since the entire length of the tube structure is excited, a tube of greater length increases residence times of the particles in the acoustic field in the fluid generated by the elongated structure.

In one embodiment, the dimensions of first transducer 20 were 30 mm long, 3 mm thick, and 1.5 mm wide, with a corresponding thickness mode resonance of 420 kHz determined by measurement with an impedance analyzer. First transducer 20 used in this example was lead zirconate titanate, but may be selected from any transducer known to those practiced in the art, to include: piezoceramic, piezosalt, piezopolymer, piezocrystal, magnetostrictive, or electromagnetic transducers. The resonance of the system, defined as the frequency of forced oscillation, (marked by an increase in the oscillatory energy absorbed by and transferred into the system) was determined to be approximately 417 kHz by scanning the drive frequency of function generator 60 to find the point of particle concentration observed within glass tube 10.

Second transducer 40, also connectively attached to glass tube 10, was used for tuning the drive frequency to the resonance of the structural acoustic mode of the system. Note that in another embodiment, second transducer 40 may be used to provide electronic feedback to maintain resonant frequency and automatic ambient temperature compensation of the system. The tuning signal was viewed on oscilloscope 50. Tuning was achieved by varying the drive frequency to maximize the received tuning signal as observed on oscilloscope 50. Second transducer 40 may also be selected from piezoceramic, piezosalt, piezopolymer, piezocrystal, magnetostrictive, or electromagnetic transducers.

First transducer 20 was driven using 30V function generator 60 that provided a radio frequency electrical signal, which was then passed through 75 W power amplifier 70 to amplify the signal. Note that power amplifier 70 is not needed to practice the present invention, but is included in a preferred embodiment. Any voltage source circuit known to those skilled in the art that is capable of producing a variety of voltage waveforms of varying frequencies may be used for function generator 60. Typical drive signal amplitudes into first transducer 20 were 10-12 Vpp and 80 mA. The signal current was measured as a voltage across 10-ohm resistor 80 in series with first transducer 20.

Ten-micron particles, with a standard deviation of 0.7 microns, were diluted to a concentration of approximately 0.025% by volume in distilled water, and then flowed through glass tube 10 at a flow rate of 5-25 mm/s using a gravity feed water system. The liquid was not degassed in order to most accurately mimic the conditions expected in a microfluidic system, and was only minimally stirred in order to maintain suspension of the particles in solution while within the feed water reservoir.

The outer boundary surface displacement of glass tube 10 was calculated using the theoretical model described above. Particle concentration to the central axis of the tube occurs when the coupled structure/cavity mode becomes dipole in character as defined by the external surface displacements of the tube. Calculations determined this mode to occur at frequency 417 kHz for the configuration described. The material properties of the glass were determined by matching index of refraction, density, longitudinal sound speed, and coefficient of thermal expansion to soda lime glass. A longitudinal sound speed of 5900 m/s, shear sound speed of 3300 m/s, and density of 2.43 g/cm$^3$ were used for the glass. The values of sound speed and density of air used in the calculations were 340 m/s and 10$^{-6}$ g/cm$^3$ respectively. Water was assumed to have sound speed of 1487 m/s and density of 1 g/cm$^3$. Pre-experimental modeling of the system allows for accurate identification of particular structural modes with maximal acoustic concentration efficiency.

Figure 3:
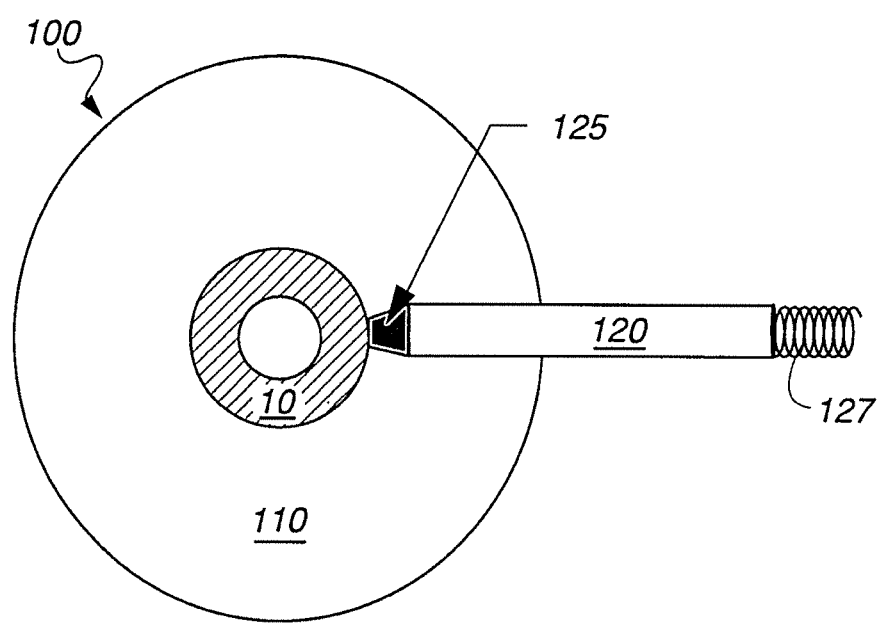
FIG. 3 pictorially illustrates an angle scan apparatus used to measure surface vibration of a glass tube used to practice the present invention.

Referring to FIG. 3, angle scanning apparatus 100 was used to determine the surface vibration of glass tube 10, allowing verification of the desired mode of excitation on the outer boundary of glass tube 10. Glass tube 10 was mounted to computer controlled angular stepper motor stage 110 and probed with a narrow transducer (pinducer) 120. Half hemisphere of solder 125 was affixed to pinducer 120 to assure point contact with glass tube 10, thus minimizing the angular integration of the signal. To maintain constant contact with glass tube 10, pinducer 120 was mounted on spring 127.

Figure 4:
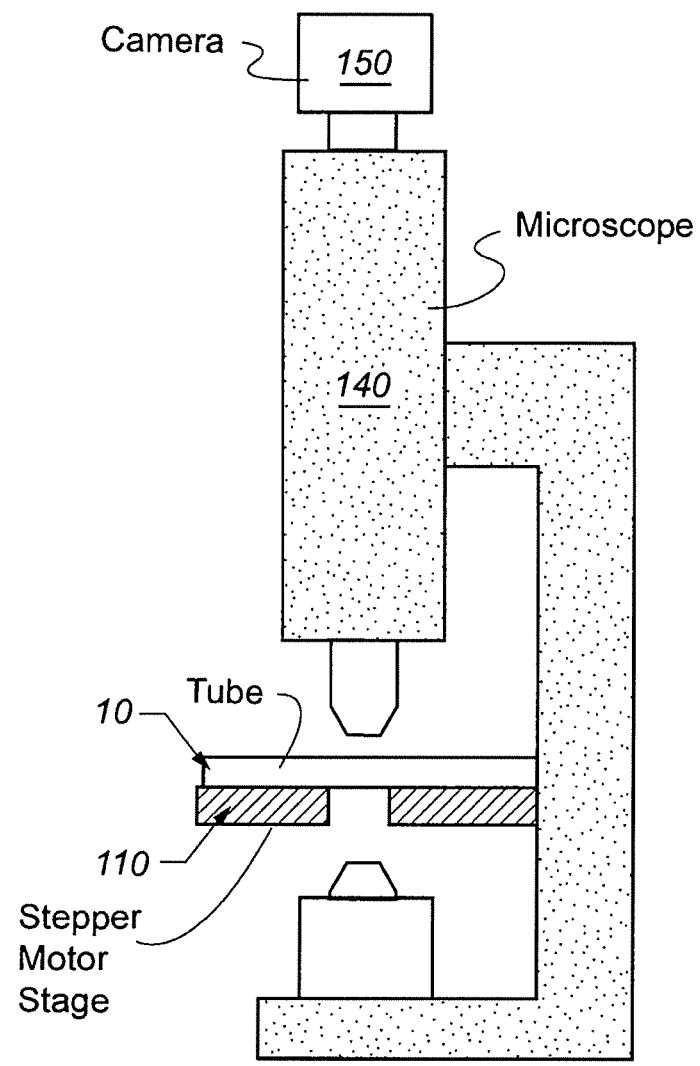
FIG. 4 pictorially illustrates a bottom-illuminated microscope used to image the particle concentration pattern within water flowing through a glass tube used to practice the present invention.

Referring to FIG. 4, computer controlled 12-bit digital oscilloscope 50 was used for data collection. Tube 10 was measured using the above apparatus for both air-filled and water-filled cases. Images of the resulting concentration pattern were taken using bottom-illuminated microscope 140 and 1280×1024 12-bit digital camera 150.

Theory predicted and experimental measurements were taken first with glass tube 10 filled with air and then with glass tube 10 filled with flowing water, in order to compare the outer boundary states of both configurations.

Figure 5:
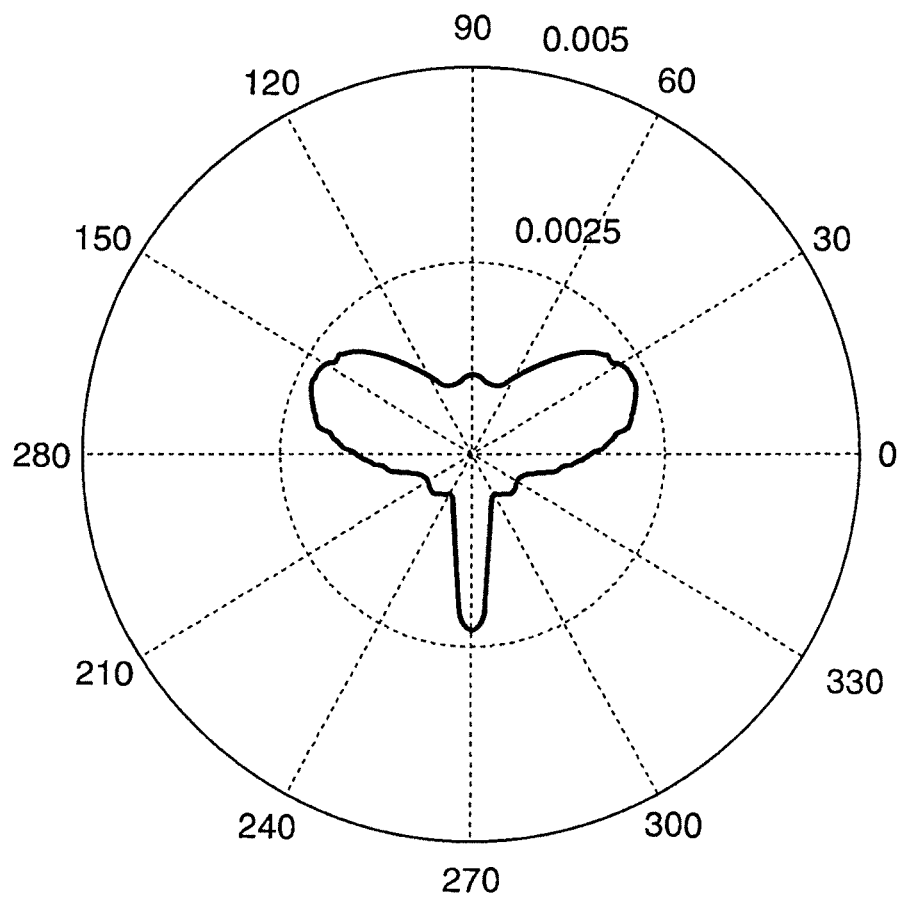
FIG. 5 graphically shows predicted outer boundary surface displacement of an air filled glass tube.
Figure 6:
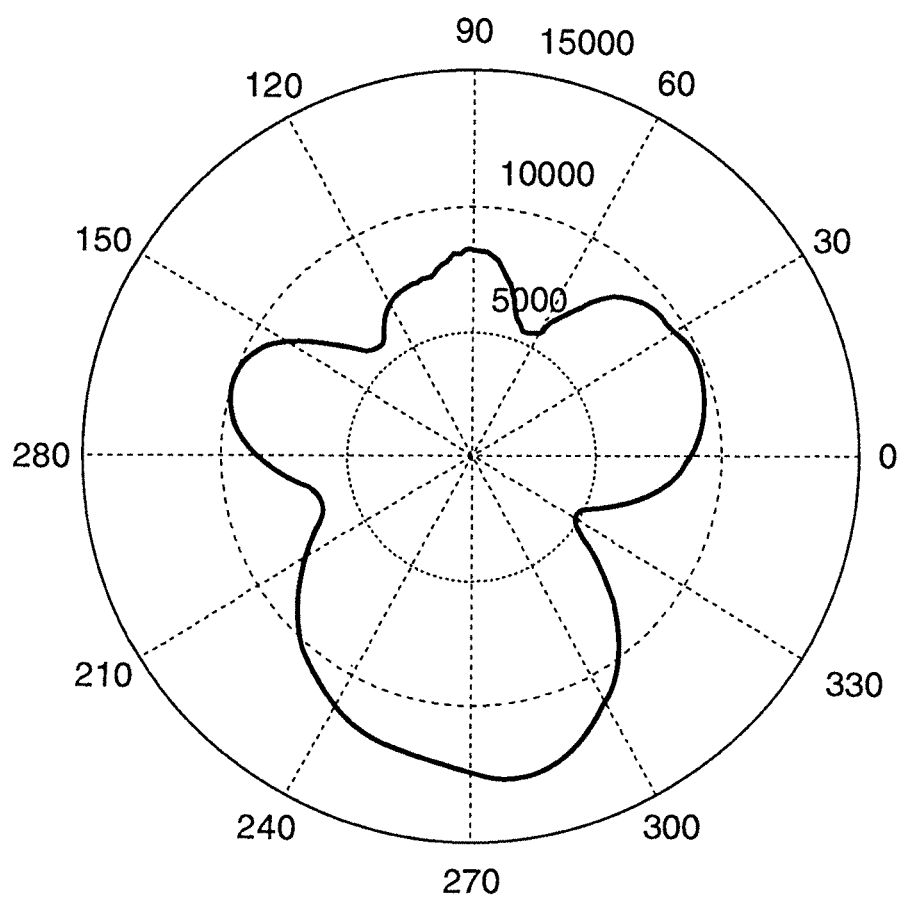
FIG. 6 graphically shows experimentally measured outer boundary surface displacement of an air filled glass tube.

FIG. 5 shows the theory predicted surface displacement of the outer boundary of an air filled glass tube 10. The corresponding measured surface displacement found in the experiment is shown in FIG. 6. The demarcations around the polar axis are given in degrees, while the radial axis indicates the absolute value of displacement in both figures. Three primary lobes at approximately 120-degree relative angles and a directly opposite smaller lobe are seen in both the calculated and measured result. The greater angular spread in the measured data was due to width of angular coupling of the drive transducer 20.

Figure 7:
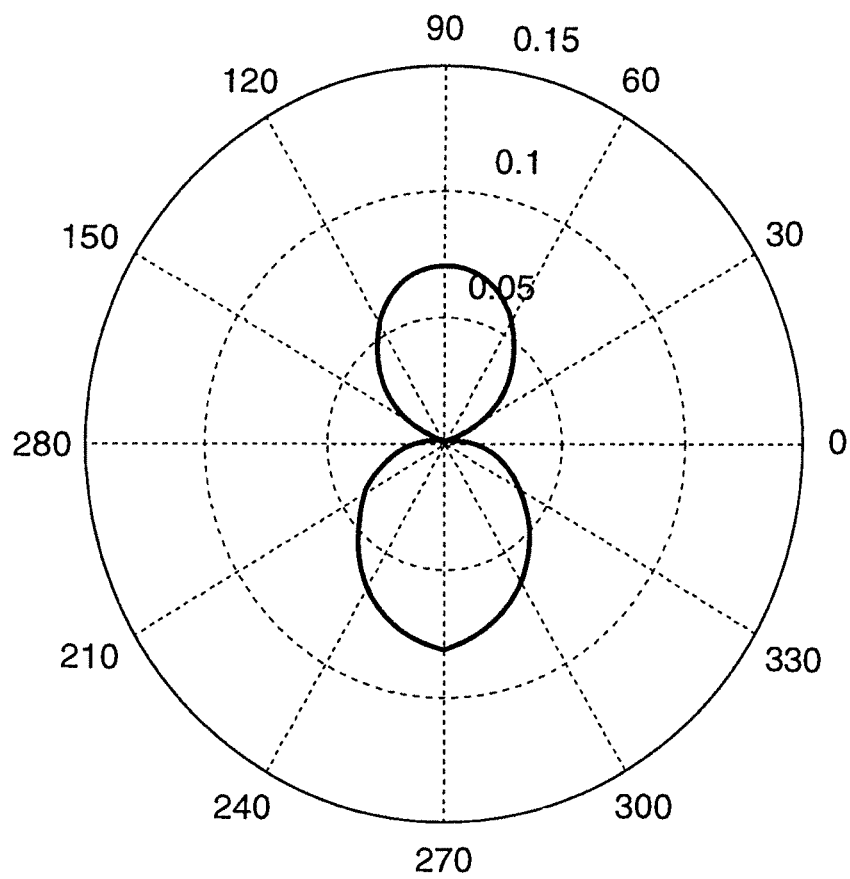
FIG. 7 graphically shows predicted outer boundary surface displacement for a water filled glass tube.
Figure 8:
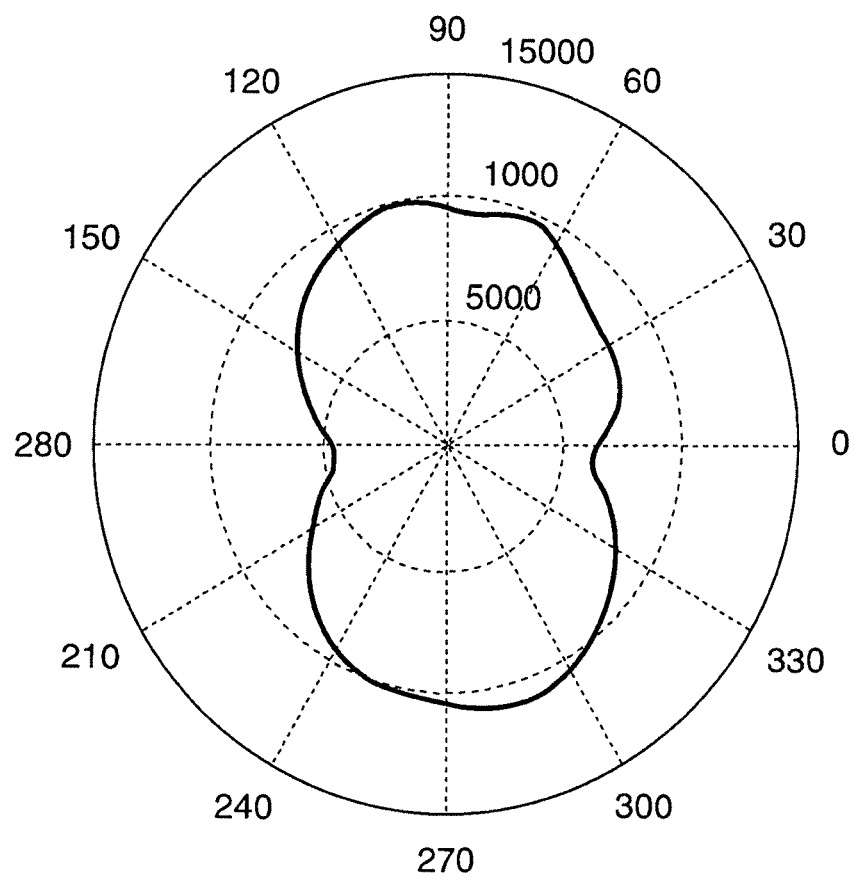
FIG. 8 graphically shows experimentally measured outer boundary surface displacement for a water filled glass tube.

When glass tube 10 was filled with flowing water, the four lobed external displacement shown in FIG. 6 collapsed to a strong dipole, as can be seen in both the theory predicted result shown in FIG. 7, and the experimental outer boundary displacement shown in FIG. 8. Thus, it was concluded that the preferred mode of vibration for a cylindrical tube is a dipole.

Figure 9:
FIG. 9 is a micrograph of 10-micron particles within water flowing though a glass tube prior to practicing the present invention.
Figure 10:
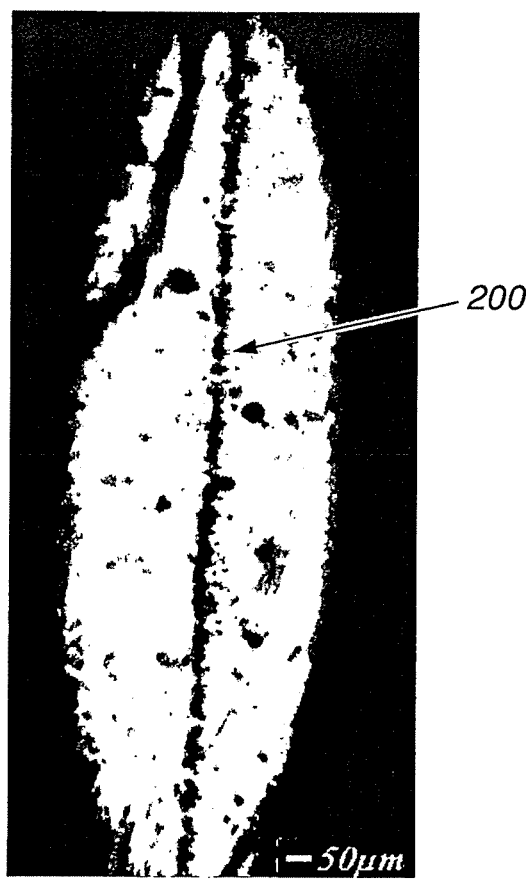
FIG. 10 is a micrograph showing the concentration of 10-micron particles within a fluid passing though a glass tube while practicing the present invention.

Particles (latex microspheres) were then added to the flowing water. FIG. 9 shows the particle concentration pattern prior to energizing first transducer 20. Tube 10 was then subjected to 0.8-0.9 W with drive transducer 60. Referring to FIG. 6, it took approximately 5 seconds to form particle concentration line 200 that is only a few particle diameters across.

Various concentrations of particles ranging from 0.02% to 0.2% by weight were investigated. No significant differences were observed in concentration times, but experiments involving concentrations of particles greater than 0.1% by weight showed increased agglomeration due to the secondary forces discussed earlier. Note, the agglomerations were also concentrated at the center, but did not disassociate at power levels less than 1 W.

Particle concentration was observed using low input power, without the necessity of careful transducer/system alignment inherent in devices described in prior art. Traditionally, when opposing transducers are used in a cavity, the position of the transducer is used to adjust the resonance of the cavity. Over time, the transducers misalign from small jolts to the system. Additionally, the traditional methods of acoustic concentration utilize quarter wave matching layers, half-wavelength cavities and require careful alignment for an axially non-symmetric system. Using an inherently symmetric geometry for the system eliminates the need for careful alignment.

In traditional acoustic separation and manipulation techniques, the acoustic field is only present directly in line with the exciting transducer. In flowing systems, the residence time of the particles in the acoustic field is limited by the physical size of the transducer. This limitation demands that larger amounts of energy be pumped into the transducer to compensate for this short interaction time scale. This large energy pumping into the flow volume leads to large temperature fluctuations, cavitation, and convection.

However, in the present invention, by exciting the entire tube structure, the active region is not limited by the size of the transducer, but rather by the size of the structure. The acoustic field is dispersed throughout this larger volume leading to significantly lower acoustic energy densities within the flow stream. Thus, temperature effects are not induced and residence times of the particle in the field are dramatically increased.

Correspondence of concentration to a dipole mode of the system was shown. Reduction of the elastodynamic equation to two dimensions has proved to be a reasonable simplification. The validity of the global matrix model for the vibration has also been demonstrated. Application of this model to determining optimal material properties and geometric parameters for particle concentration has been proved.

EXAMPLE 2

Figure 11:
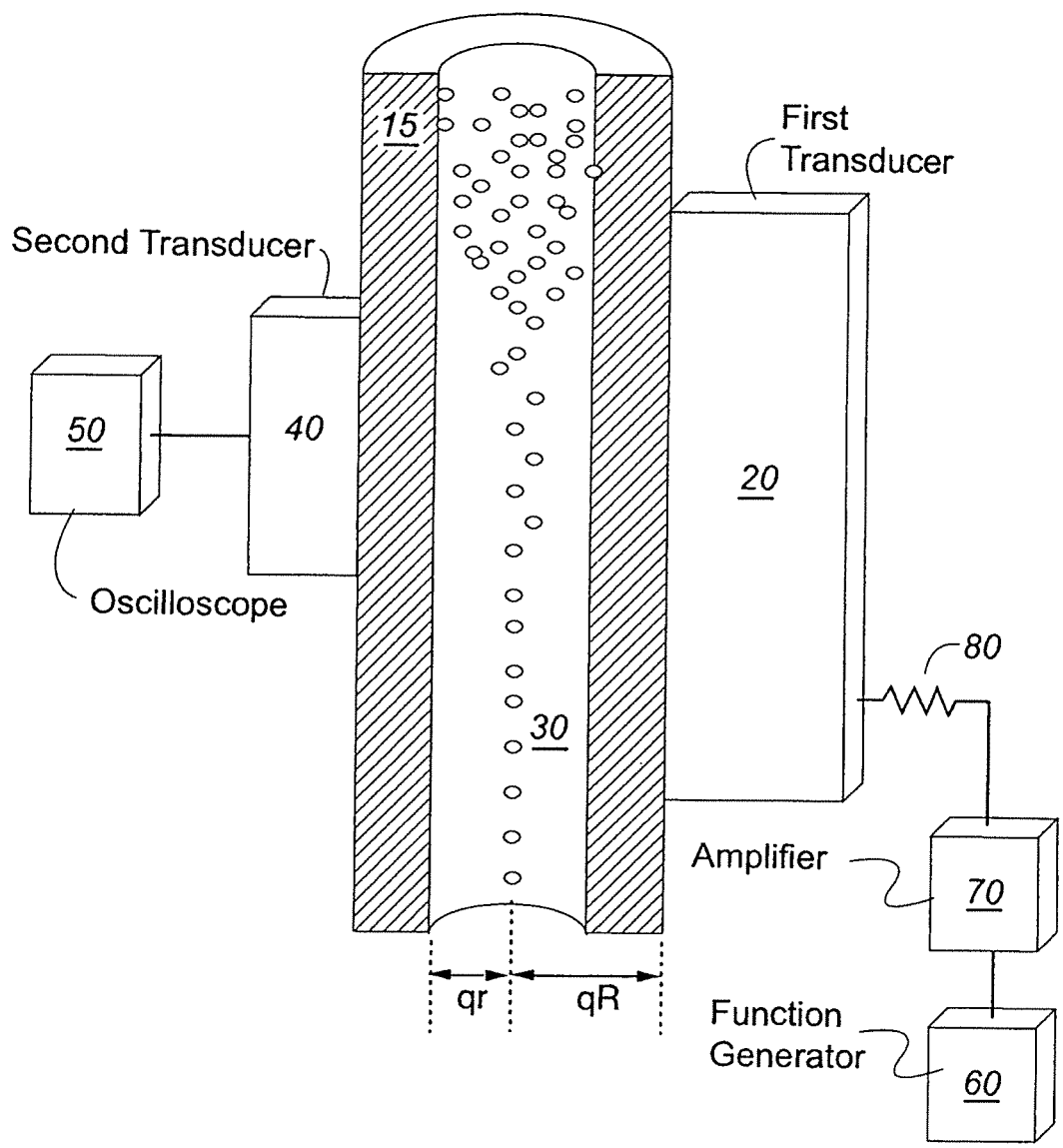
FIG. 11 pictorially illustrates an experimental setup using a quartz tube for practicing the present invention.

Referring now to FIG. 11, thick-walled, cylindrical quartz tube 15 was tested for comparison with the glass tube in Example 1. Quartz tube 15 had inner diameter qr of 2.0 mm and outer diameter qR of 7.85 mm. First transducer 20 was again, connectively attached, axially to quartz tube 15 as in Example 1.

Figure 12:
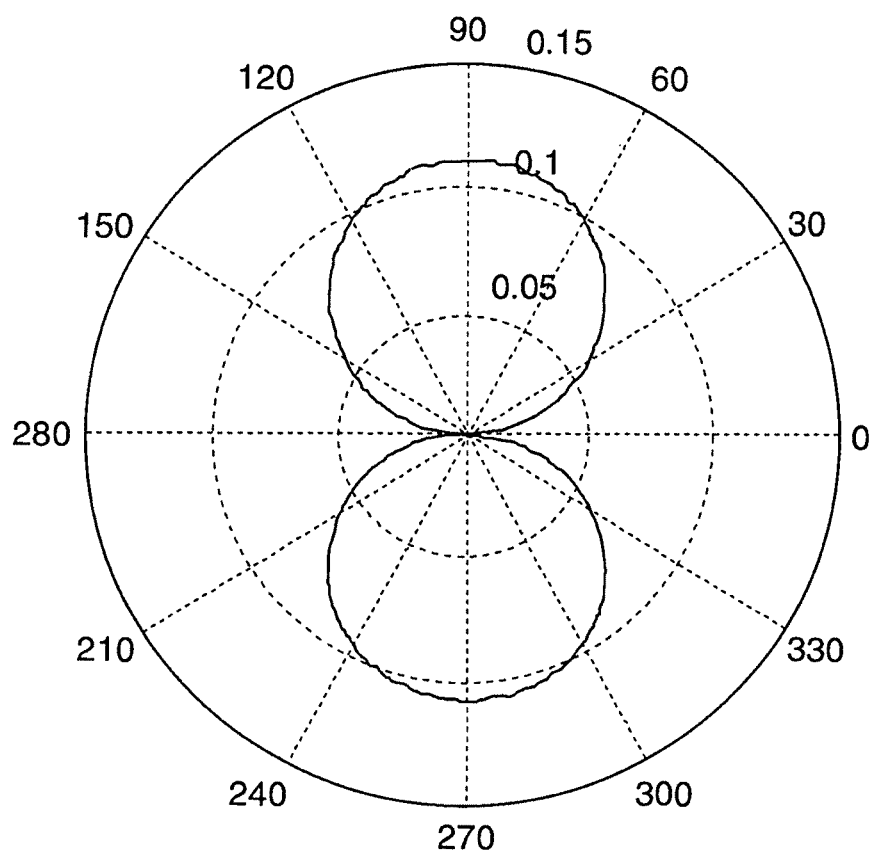
FIG. 12 graphically shows predicted outer boundary surface displacement for a water filled quartz tube.
Figure 13:
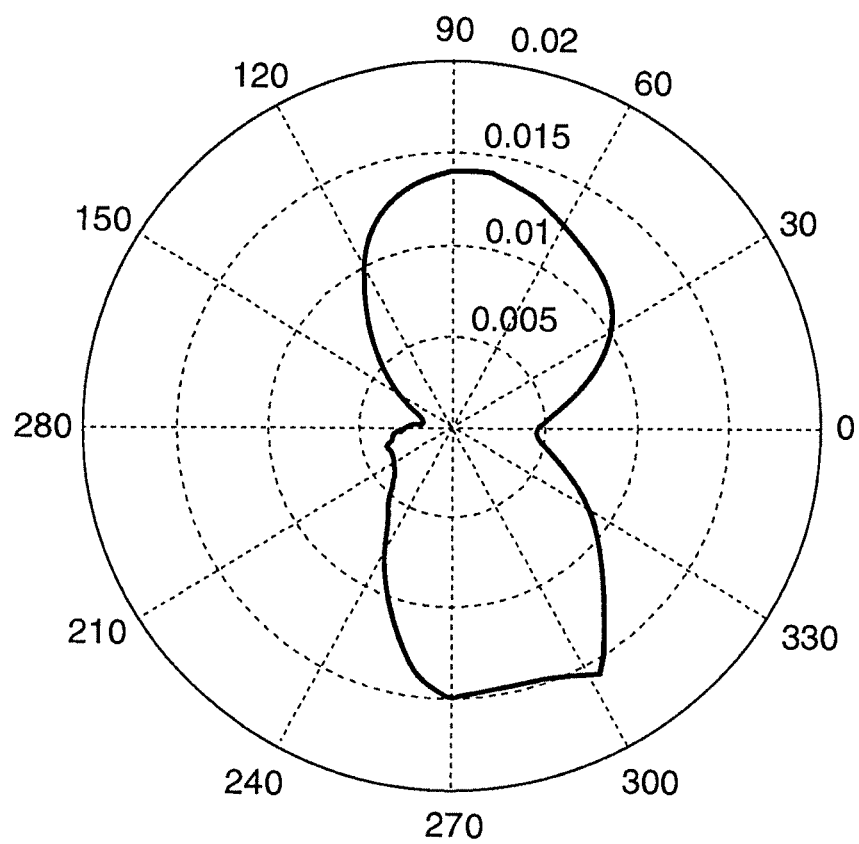
FIG. 13 graphically shows experimentally measured outer boundary surface displacement for a water filled quartz tube.

The material properties of quartz tube 15 were: longitudinal sound speed of 5700 m/s, transverse sound speed of 2650 m/s and density of 2.65 g/cm$^3$. The same properties of air and water as used in Example 1 were used for Example 2. The theoretical model outer boundary surface vibration predicted a dipole at 462 kHz for quartz tube 15, shown in FIG. 12. Actual surface vibration measurement yielded the results shown in FIG. 13. As can be seen, there was good correspondence between the predicted and experimental results. It is worth noting that the predicted strength of dipole vibration in quartz, as shown in FIG. 12, was greater than that of glass, as shown in FIG. 9. Thus, it is to be expected that, for equal power input, quartz tubing will demonstrate a tighter focusing of the particles within the flowing water.

Figure 14:
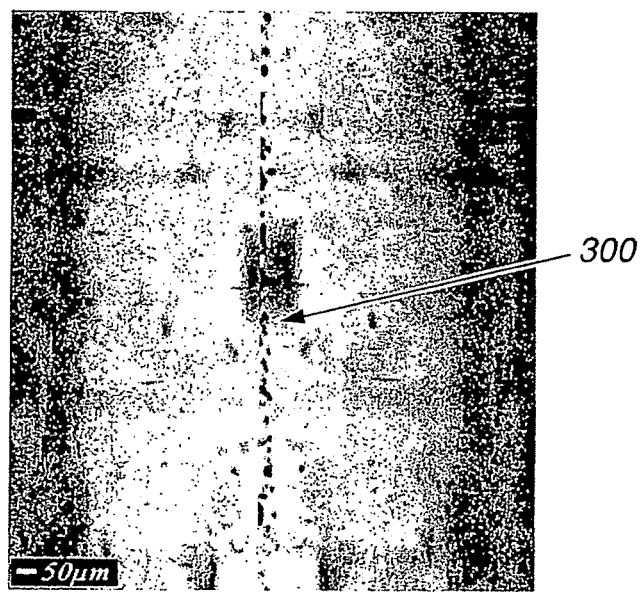
FIG. 14 is a micrograph of 10-micron particles concentrated within water flowing through a quartz tube at 462 kHz.

In order to verify this assertion between dipole vibration and concentration, particles were fed through the quartz tubing and the concentration pattern at 462 kHz was imaged. A micrograph of the resulting particle concentration pattern is shown in FIG. 14. Note the dipole does correspond to a frequency at which concentration takes place, and, furthermore, concentrated particles 300 form a more focused line using quartz versus glass.

Application

The most common premise for low power acoustic concentration is the requirement of quarter wave matching layers. In this type of system, the incident acoustic disturbance is resonantly amplified in the matching layers yielding higher energy transmission efficiencies. However, the inherent alignment problems of either planar or confocal geometries, even in the traveling wave case, for proper positioning, make the process more difficult.

The creation of strongly exciting cavity modes, created by driving at far below quarter wave thickness of a cylinder wall, offers some intriguing possibilities for applications. For example, the ability to discriminate, analyze, and quantify distinct populations of biological cells/ cell organelles has become increasingly important with the growing trend to focus biological studies on various cell types. Flow based cytometry and cell sorting are unique techniques that permit the identification, analysis, and purification of cells based on their expression of specific chemical markers. Furthermore, flow cytometry analysis of biochemical reactions on both cells and arrays of microspheres is a burgeoning field that is becoming widely used in biomedical, biochemical and genomic assays.

Figure 15:
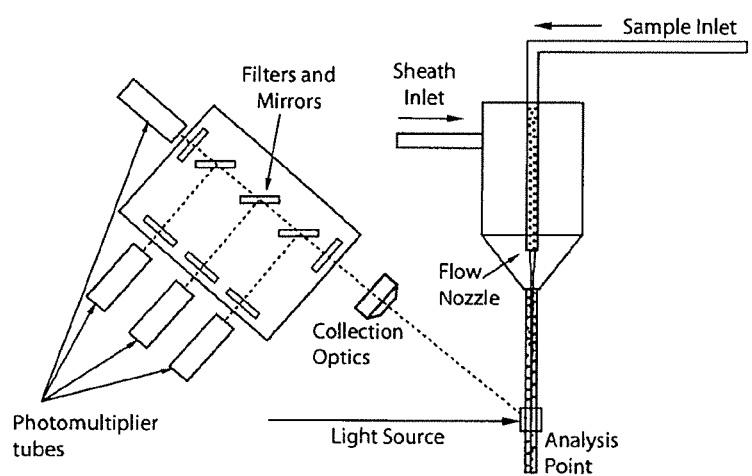
FIG. 15 pictorially illustrates a prior art conventional flow cytometer setup.

The very fine positioning provided by hydrodynamic focusing of the present invention is a critical application to precise measurements using a flow cytometer. Referring to FIG. 15, a conventional flow cytometer uses hydrodynamic focusing to generate a narrowly focused, concentrated sample stream of analytes (5-10 µm in diameter) moving at a high linear velocity (1-10 m/s), which is subjected to tightly focused (10-100 µm diameter) laser beams (or other tightly focused light source such as an arc lamp). Within the interrogation volume, formed by the intersection of the laser and the sample stream, light scatter along with several wavelength bands of fluorescence from the interaction with analytes are collected using high Numerical Aperture optics (e.g. microscope objectives or aspheric lenses) and sensitive optical detectors such as photomultiplier tubes (PMTs), avalanche photodiodes (APDs), photodiodes, and array based detectors such as CCD or CMOS array systems. The collected wavelength bands are then compared to a library of wavelength bands associated with known elements and molecules to identify the chemical composition of the analytes.

Analytes under analysis, like cells and microspheres (~10 µm in diameter), largely exclude free fluorophores from the interrogation volume. Therefore, background from unbound fluorescent probes is low, which allows sensitive measurement of particle-associated probes without separation steps. Flow cytometers can detect as little as a few hundred fluorophores at conventional flow rates (m/s), and single fluorophores with reduced flow rates (cm/s). The high linear velocity and small interrogation volume of conventional cytometers results in transit times of a few µs, requiring the use of high speed analog-to-digital converters (ADCs), operating at rates as fast as 20 MHz, to record the fluorescence and scatter signals. Note that for practitioners of the art, additional modalities, such as collection of Raman light scatter and magnetic moment detection with flow cytometers equipped with a superconducting quantum interference device (SQUID) or giant magnetoresistive (GMR) detector, may also be utilized.

Figure 16:
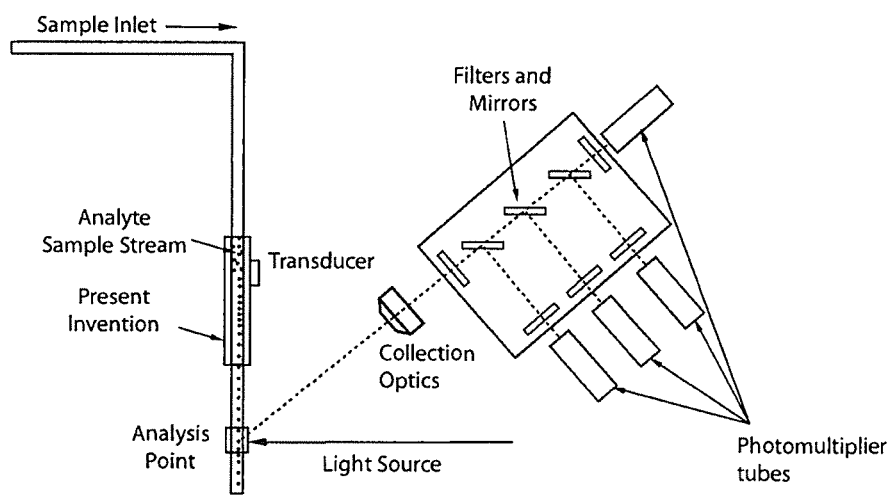
FIG. 16 pictorially illustrates a flow cytometer setup using the present invention.

The present invention may be used to acoustically focus analytes for analysis rather than using conventional hydrodynamic focusing. Acoustic focusing eliminates the need for a hydrodynamic sheath, as well as allowing for high analysis rates at lower linear velocities. Referring now to FIG. 16, in an acoustic focusing flow cytometer, the present invention is used in place of the hydrodynamic focusing nozzle of conventional cytometers to achieve a tightly focused, concentrated sample stream of analytes. Thus, the sample stream is interrogated in an identical fashion to conventional flow cytometers, but does not require sheath flow and associated equipment to focus the sample stream, allowing for increased instrument portability and reduced consumable costs.

Figure 17A:
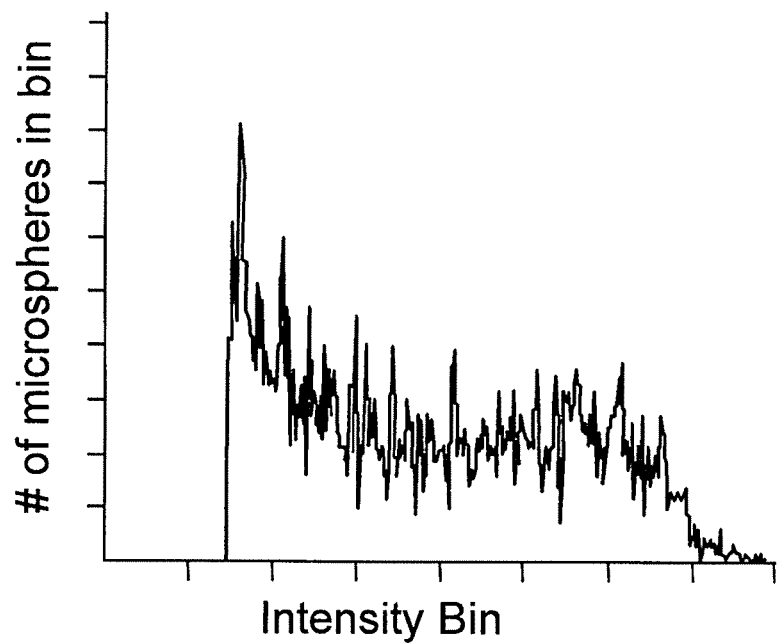
FIGS. 17a and 17b graphically show one dimensional histograms of the fluorescence collected from uniformly stained fluorescent microspheres in unfocused (17a) and acoustically focused (17b) fluid streams.
Figure 17B:
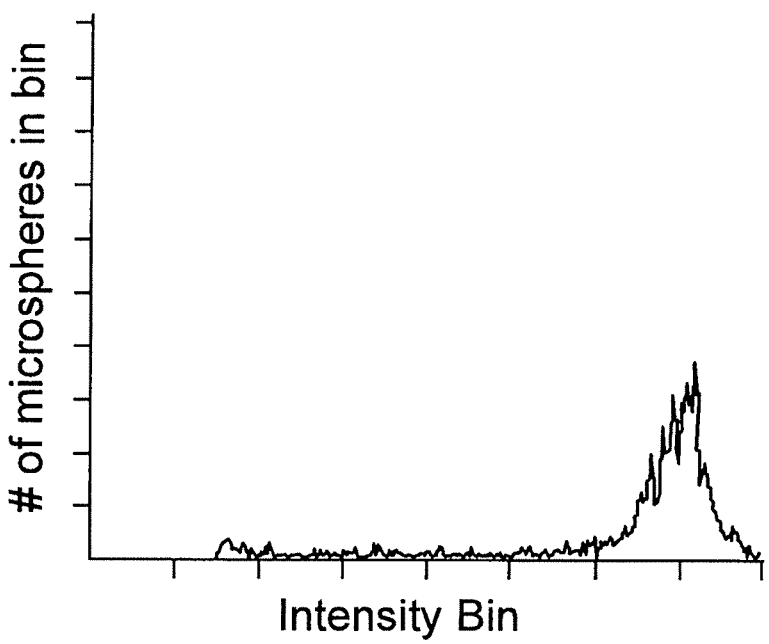

Results demonstrating acoustic focusing in a flow cytometer without sheath flow, as shown in FIG. 16, are shown in FIGS. 17a and 17b. FIG. 17a graphically shows a one-dimensional histogram of measured fluorescence collected from uniformly stained fluorescent microspheres in an unfocused fluid stream. FIG. 17b graphically shows a one-dimensional histogram of measure fluorescence collected from uniformly stained fluorescent microspheres in an acoustically focused fluid stream practicing the present invention. The x-axis corresponds to measured fluorescence intensity bins and the y-axis corresponds to the number of particles in each of the bins. A laser was used to illuminate the uniformly stained fluorescent particles (10 micron diameter) in a cylindrical cavity.

FIG. 17a shows that, because the microspheres are not focused into a particular region of the flowing stream, they are excited by varying intensities of the focused laser beam as it traverses flowing stream. The inconsistent illumination is due to random positioning as exhibited by the high degree of variation in the emitted fluorescence. The wide distribution of fluorescence values demonstrates that the microspheres are randomly positioned in the sample stream.

In comparison, FIG. 17b graphically shows acoustic radiation pressure provided by the present invention aligning the subject fluorescent microspheres within the fluid stream, ensuring that all microspheres experience uniform illumination. FIG. 17b shows this in that the distribution of fluorescence intensities forms a tight peak, indicating that the microspheres are excited with similar intensities of focused laser light. This result demonstrates that acoustic radiation pressure can be used to align analytes into a sample core similar in fashion to hydrodynamic focusing used in prior art flow cytometers.

Furthermore, as the present invention both focuses and concentrates analytes; it is possible to analyze high numbers of analytes at low linear velocities. For example, a volumetric sample delivery rate of 75 µl/minute through a 200 µm diameter channel yields a core velocity (2×average velocity) of 8 cm/s. This is much slower than a traditionally focused flow cytometer (usually in the 1 m/s to 10 m/s range). Thus, use of the present invention yields a transit time of about 250 µs through a 20 µm interrogation volume. This slow transit time (~20 to 100 times slower than conventional systems) allows for analyte analysis rates using lower speed data acquisition systems that are less expensive, smaller, and that require less power. The extended transit time provided by the present invention allows for longer collection of optical signals that provide higher sensitivity measurements than conventional systems.

Additionally, the concentration effect of acoustic focusing allows for the analysis of very dilute samples that would be difficult to analyze due to time constraints using conventional flow cytometry systems. For example, using a large diameter focusing chamber, samples can be delivered at ml/minute volumetric flow rates. This is a very high sample delivery rate compared to most conventional hydrodynamic flow systems (µl/minute), which enables the analysis of highly dilute samples commonly found in bioforensics and other applications. By increasing the diameter of the flow chamber even more dilute samples can be effectively analyzed. In fact, the diameter of the focusing chamber may be tailored to fit the expected concentration of the samples to be analyzed.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for subjecting particles within a fluid to acoustic radiation pressure, said apparatus comprising:
    an inlet for accepting the fluid containing the particles therein;
    a substantially cylindrical flow chamber wherein said flow chamber accepts the fluid;
    a single acoustic signal producing transducer connectively attached axially to the flow chamber, producing acoustic radiation pressure by acoustically exciting substantially the entire length of the flow chamber; and
    said acoustic radiation pressure causing an aligning of the particles within the fluid at the central longitudinal axis of the flow chamber.

2. The apparatus of claim 1 wherein said acoustic radiation pressure concentrates the particles.

3. The apparatus of claim 1 wherein said acoustic radiation pressure positions the particles.

4. The apparatus of claim 1 wherein said acoustic radiation pressure fractionates the particles.

5. The apparatus of claim 1 further comprising a function generator outputting a radiofrequency electrical signal related to the acoustic signal producing transducer to drive the acoustic signal producing transducer.

6. The apparatus of claim 5 wherein said function generator is selected from any voltage source circuit capable of producing a variety of voltage waveforms of varying frequencies.

7. The apparatus of claim 5 further comprising a power amplifier to amplify said output of said function generator.

8. The apparatus of claim 1 further comprising a monitoring transducer configured to monitor a frequency of the acoustic radiation pressure.

9. The apparatus of claim 8 wherein said monitoring transducer monitors said acoustic radiation pressure to maintain resonant frequency.

10. The apparatus of claim 8 wherein said monitoring transducer monitors said acoustic radiation pressure to compensate for a temperature fluctuation.

11. The apparatus of claim 8 wherein said monitoring transducer is selected from the group consisting of a piezoceramic, piezosalt, piezopolymer, piezocrystal, magnetostrictive, and electromagnetic transducer.

12. The apparatus of claim 1 wherein said apparatus does not contain a hydrodynamic sheath.

13. The apparatus of claim 1 wherein said acoustic radiation pressure agglomerates the particles.

14. The apparatus of claim 1 wherein the central longitudinal axis of the flow chamber is vertically oriented.

15. A method for subjecting particles within a fluid to acoustic radiation pressure, the method comprising:
    flowing the fluid with particles therein into a substantially cylindrical flow chamber;
    subjecting the fluid to the acoustic radiation pressure using a single acoustic signal producing transducer connectively attached axially to the flow chamber and configured to acoustically excite substantially the entire length of the flow chamber; and
    causing aligning of the particles within the fluid at the central longitudinal axis of the flow chamber.

16. The method of claim 15 further comprising concentrating the particles.

17. The method of claim 15 further comprising positioning the particles.

18. The method of claim 15 further comprising fractionating the particles.

19. The method of claim 15 further comprising inducing an outer boundary surface displacement.

20. The method of claim 19 further comprising monitoring the outer boundary surface displacement.

21. The method of claim 15 further comprising adjusting the frequency of the acoustic radiation pressure to maintain a resonant frequency.

22. The method of claim 15 further comprising adjusting the frequency of the acoustic radiation pressure to adjust for a temperature change.

23. The method of claim 15 further comprising moving the particles to an antinodal position.

24. The method of claim 15 further comprising moving the particles to a nodal position.

25. The method of claim 15 further comprising transforming a radio frequency electrical signal to an acoustic signal.

26. The method of claim 15 further comprising converting an acoustic signal to acoustic radiation pressure within the flow chamber.

27. The method of claim 15 not using a hydrodynamic sheath.

28. The method of claim 15 furthering comprising collecting Raman signals from the particles.

29. The method of claim 15 wherein the flowing the fluid is in a velocity range of from about 0.5 cm/s to about 8 cm/s.

30. The method of claim 15 wherein the flowing the fluid is in a velocity range of from about 0.5 cm/s to about 2.5 cm/s.

31. The method of claim 15 wherein the central longitudinal axis of the flow chamber is vertically oriented.

* * * * *